United States Patent
Donohue et al.

(10) Patent No.: US 10,330,691 B2
(45) Date of Patent: Jun. 25, 2019

(54) LIGHT-BLOCKING SYSTEM FOR A DIAGNOSTIC ANALYZER

(71) Applicant: Abbott Laboratories, Abbott Park, IL (US)

(72) Inventors: Joseph P. Donohue, Pleasant Prairie, WI (US); Ryan Patrick Johnson, Bedford, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 47 days.

(21) Appl. No.: 15/339,433

(22) Filed: Oct. 31, 2016

(65) Prior Publication Data

US 2017/0045540 A1     Feb. 16, 2017

Related U.S. Application Data

(62) Division of application No. 14/214,190, filed on Mar. 14, 2014, now Pat. No. 9,513,303.

(Continued)

(51) Int. Cl.
*G01N 35/04* (2006.01)
*G01N 35/00* (2006.01)
(Continued)

(52) U.S. Cl.
CPC .......... *G01N 35/021* (2013.01); *G01N 21/76* (2013.01); *G01N 35/0099* (2013.01);
(Continued)

(58) Field of Classification Search
CPC ... G01N 35/00029; G01N 35/00; G01N 35/04
(Continued)

(56) References Cited

U.S. PATENT DOCUMENTS

| | | | |
|---|---|---|---|
| 2,725,971 | A | 12/1955 | Clark-Riede |
| 2,770,352 | A | 11/1956 | Moller |

(Continued)

FOREIGN PATENT DOCUMENTS

| | | |
|---|---|---|
| CA | 2254017 | 5/2000 |
| CA | 2497397 | 2/2004 |

(Continued)

OTHER PUBLICATIONS

International Search Report and Written Opinion for PCT/US14/29462, dated Sep. 30, 2014.

*Primary Examiner* — Christine T Mui
(74) *Attorney, Agent, or Firm* — Klintworth & Rozenblat IP LLP

(57) ABSTRACT

A diagnostic analyzer includes a track, a light-blocking member, a motor, and an optical testing device. The track moves a reaction vessel held by the track. The light-blocking member is disposed adjacent to the track. The light-blocking member moves from a first position apart from the track to a second position closer to the track. When the light-blocking member is disposed in the first position a sample contained within the reaction vessel held by the track is exposed to light. When the light-blocking member is disposed in the second position the sample contained within the reaction vessel held by the track is blocked from exposure to the light. The motor moves the light-blocking member between the first and the second positions. The optical testing device is disposed adjacent to the track for optically testing the sample contained within the reaction vessel held by the track when the at least one light-blocking member is disposed in the second position.

15 Claims, 15 Drawing Sheets

Related U.S. Application Data

(60) Provisional application No. 61/790,480, filed on Mar. 15, 2013.

(51) Int. Cl.
    *G01N 35/02* (2006.01)
    *G01N 21/76* (2006.01)

(52) U.S. Cl.
    CPC ............. *G01N 35/02* (2013.01); *G01N 35/04* (2013.01); *G01N 2035/0429* (2013.01); *G01N 2201/0642* (2013.01); *G01N 2201/0648* (2013.01); *Y10T 436/113332* (2015.01); *Y10T 436/114165* (2015.01)

(58) Field of Classification Search
    USPC ..................................................... 422/63, 50
    See application file for complete search history.

(56) References Cited

U.S. PATENT DOCUMENTS

| | | |
|---|---|---|
| 2,807,350 A | 9/1957 | Black, Jr. |
| 2,891,668 A | 6/1959 | Hunt |
| 3,143,201 A | 8/1964 | Wyle |
| 3,350,946 A | 11/1967 | Isreeli |
| 3,432,271 A | 3/1969 | Wasilewski |
| 3,481,709 A | 12/1969 | Slone |
| 3,511,613 A | 5/1970 | Jones |
| 3,532,469 A | 10/1970 | Vicario |
| 3,536,449 A | 10/1970 | Astle |
| 3,622,279 A | 11/1971 | Moran |
| 3,623,515 A | 11/1971 | Gilson |
| 3,635,394 A | 1/1972 | Natelson |
| 3,644,095 A | 2/1972 | Bechtler |
| 3,660,638 A | 5/1972 | Oberli |
| 3,687,632 A | 8/1972 | Natelson |
| 3,716,338 A | 2/1973 | Moran |
| 3,722,790 A | 3/1973 | Natelson |
| 3,723,066 A | 3/1973 | Moran |
| 3,728,079 A | 4/1973 | Moran |
| 3,728,080 A | 4/1973 | Moran |
| 3,762,879 A | 10/1973 | Moran |
| 3,785,773 A | 1/1974 | Rohrbaugh |
| 3,825,410 A | 7/1974 | Bagshawe |
| 3,826,622 A | 7/1974 | Natelson |
| 3,841,838 A | 10/1974 | Natelson |
| 3,882,619 A | 5/1975 | Durand |
| 3,888,629 A | 6/1975 | Bagshawe |
| 3,897,216 A | 7/1975 | Jones |
| 3,932,131 A | 1/1976 | Rolfo-Fontana |
| 3,985,508 A | 10/1976 | Williams |
| 3,994,594 A | 11/1976 | Sandrock |
| 4,039,288 A | 8/1977 | Moran |
| 4,055,396 A | 10/1977 | Meyer |
| 4,140,018 A | 2/1979 | Maldarelli |
| 4,158,545 A | 6/1979 | Yamashita et al. |
| 4,168,955 A | 9/1979 | Allington |
| 4,190,420 A | 2/1980 | Covington |
| 4,244,459 A | 1/1981 | Garrett |
| 4,251,159 A | 2/1981 | White |
| 4,260,581 A | 4/1981 | Sakurada |
| 4,278,437 A | 7/1981 | Haggar |
| 4,315,891 A | 2/1982 | Sakurada |
| 4,363,781 A | 12/1982 | Akamatsu |
| 4,363,782 A | 12/1982 | Yamashita |
| 4,366,119 A | 12/1982 | Takeuchi |
| 4,413,534 A | 11/1983 | Tomoff |
| 4,459,864 A | 7/1984 | Cirincione |
| 4,495,149 A | 1/1985 | Iwata |
| 4,527,438 A | 7/1985 | Fosslien |
| 4,537,231 A | 8/1985 | Hasskamp |
| 4,600,120 A | 7/1986 | Sabo |
| 4,609,017 A | 9/1986 | Coulter |
| 4,623,008 A | 11/1986 | Shibata |
| 4,634,575 A | 1/1987 | Kawakami |
| 4,664,885 A | 5/1987 | Minekane et al. |
| 4,678,752 A | 7/1987 | Thorne |
| 4,692,308 A | 9/1987 | Riley et al. |
| 4,694,951 A | 9/1987 | Gibbemeyer |
| 4,713,219 A | 12/1987 | Gerken |
| 4,718,319 A | 1/1988 | Bajohr |
| 4,719,087 A | 1/1988 | Hanaway |
| 4,720,463 A | 1/1988 | Farber |
| 4,731,225 A | 3/1988 | Wakatake |
| 4,751,186 A | 6/1988 | Baisch |
| 4,797,258 A | 1/1989 | Mochida |
| 4,815,625 A | 3/1989 | Filhol |
| 4,818,883 A | 4/1989 | Anderson |
| 4,853,188 A | 8/1989 | Toya |
| 4,855,110 A | 8/1989 | Marker, Jr. |
| 4,861,553 A | 8/1989 | Mawhirt |
| 4,861,554 A | 8/1989 | Sakuma |
| 4,900,513 A | 2/1990 | Barker |
| 4,931,256 A | 6/1990 | Mack et al. |
| 4,935,274 A | 6/1990 | DeBenedictis |
| 4,948,564 A | 8/1990 | Root |
| 4,970,053 A | 11/1990 | Fechtner |
| 5,005,721 A | 4/1991 | Jordan |
| 5,008,082 A | 4/1991 | Shaw |
| 5,009,942 A | 4/1991 | Benin |
| 5,035,861 A | 7/1991 | Grandone |
| 5,035,866 A | 7/1991 | Wannlund |
| 5,055,263 A | 10/1991 | Meltzer |
| 5,075,082 A | 12/1991 | Fechtner |
| 5,098,661 A | 3/1992 | Anderson |
| 5,112,574 A | 5/1992 | Horton |
| 5,125,680 A | 6/1992 | Bejean |
| 5,128,104 A | 7/1992 | Murphy |
| 5,145,646 A | 9/1992 | Tyranski |
| 5,158,895 A | 10/1992 | Ashihara |
| 5,173,741 A | 12/1992 | Wakatake |
| 5,178,834 A | 1/1993 | Kagayama et al. |
| 5,242,659 A | 9/1993 | Wurschum |
| 5,244,633 A | 9/1993 | Jakubowicz |
| 5,250,440 A | 10/1993 | Kelln |
| 5,246,665 A | 11/1993 | Hirsch |
| 5,265,655 A | 11/1993 | Hirsch |
| 5,270,011 A | 12/1993 | Altherr |
| 5,271,899 A | 12/1993 | Carbonari |
| 5,277,871 A | 1/1994 | Fujii |
| 5,290,708 A | 3/1994 | Ashihara |
| 5,306,510 A | 4/1994 | Meltzer |
| 5,316,726 A | 5/1994 | Babson |
| 5,322,668 A | 6/1994 | Tomasso |
| 5,332,549 A | 7/1994 | MacIndoe, Jr. |
| 5,364,592 A | 11/1994 | Lewis |
| 5,368,820 A | 11/1994 | Lautenschlager |
| 5,380,487 A | 1/1995 | Choperena |
| 5,380,488 A | 1/1995 | Wakatake |
| 5,422,075 A | 6/1995 | Aoki |
| 5,424,036 A | 6/1995 | Ushikubo |
| 5,445,794 A | 8/1995 | Wihlborg |
| 5,456,884 A | 10/1995 | Lewis |
| 5,482,839 A | 1/1996 | Ashihara et al. |
| 5,482,863 A | 1/1996 | Knobel |
| 5,507,410 A | 4/1996 | Clark |
| 5,511,690 A | 4/1996 | Calhoun |
| 5,518,688 A | 5/1996 | Gianino |
| 5,544,778 A | 8/1996 | Goncalves |
| 5,554,536 A | 9/1996 | Rising |
| 5,567,386 A | 10/1996 | Markin |
| 5,578,272 A | 11/1996 | Koch |
| 5,580,524 A | 12/1996 | Forrest |
| 5,582,796 A | 12/1996 | Carey |
| 5,605,665 A | 2/1997 | Clark |
| 5,623,415 A | 4/1997 | O'Bryan et al. |
| 5,628,428 A | 5/1997 | Calhoun |
| 5,632,396 A | 5/1997 | Burns |
| 5,637,275 A | 6/1997 | Carey |
| 5,645,800 A | 7/1997 | Masterson |
| 5,650,125 A | 7/1997 | Bosanquet |
| 5,653,940 A | 8/1997 | Carey |
| 5,658,799 A | 8/1997 | Choperena |
| 5,670,117 A | 9/1997 | Erb |

(56) References Cited

U.S. PATENT DOCUMENTS

| | | |
|---|---|---|
| 5,672,317 A | 9/1997 | Buhler |
| 5,679,948 A | 10/1997 | Carey |
| 5,683,659 A | 11/1997 | Hovatter |
| 5,693,292 A | 12/1997 | Choperena |
| 5,700,429 A | 12/1997 | Buhler |
| 5,720,377 A | 2/1998 | Lapeus et al. |
| 5,720,406 A | 2/1998 | Fassbind |
| 5,736,101 A | 4/1998 | Gianino |
| 5,741,708 A | 4/1998 | Carey |
| 5,753,186 A | 5/1998 | Hanley |
| 5,766,549 A | 6/1998 | Gao et al. |
| 5,772,962 A | 6/1998 | Uchida et al. |
| 5,788,928 A | 8/1998 | Carey |
| 5,800,784 A | 9/1998 | Horn |
| 5,814,276 A | 9/1998 | Riggs |
| 5,846,491 A | 12/1998 | Choperena |
| 5,849,247 A | 12/1998 | Uzan |
| 5,863,506 A | 1/1999 | Farren |
| 5,876,670 A | 3/1999 | Mitsumaki et al. |
| 5,885,529 A | 3/1999 | Babson |
| 5,885,530 A | 3/1999 | Babson |
| 5,888,825 A | 3/1999 | Carr et al. |
| 5,902,549 A | 5/1999 | Mimura et al. |
| 5,922,289 A | 7/1999 | Wong |
| 5,931,828 A | 8/1999 | Durkee |
| 5,945,071 A | 8/1999 | Ekiriwang |
| 5,952,218 A | 9/1999 | Lee |
| 5,957,264 A | 9/1999 | Carey |
| 5,959,221 A | 9/1999 | Boyd |
| RE36,341 E | 10/1999 | Howell |
| 5,963,368 A | 10/1999 | Domanik |
| 5,966,309 A | 10/1999 | O'Bryan et al. |
| 5,968,453 A | 10/1999 | Shugart |
| 5,972,295 A | 10/1999 | Hanawa et al. |
| 5,985,214 A | 11/1999 | Beckey |
| 5,985,218 A | 11/1999 | Goodale |
| 5,988,236 A | 11/1999 | Fawcett |
| 6,019,945 A | 2/2000 | Ohishi et al. |
| 6,024,204 A | 2/2000 | van Dyke, Jr. |
| 6,030,582 A | 2/2000 | Levy |
| 6,056,106 A | 5/2000 | Van Dyke, Jr. |
| 6,063,340 A | 5/2000 | Lewis et al. |
| 6,063,341 A | 5/2000 | Fassbind |
| 6,074,615 A | 6/2000 | Lewis |
| 6,074,617 A | 6/2000 | DeYoung et al. |
| 6,081,326 A | 6/2000 | Gelin |
| 6,117,391 A | 9/2000 | Bakonyi |
| 6,117,392 A | 9/2000 | Hanawa |
| 6,117,683 A | 9/2000 | Kodama |
| 6,136,273 A | 10/2000 | Banar |
| 6,146,882 A | 11/2000 | Uematsu |
| 6,149,872 A | 11/2000 | Mack et al. |
| 6,202,829 B1 | 3/2001 | van Dyke, Jr. et al. |
| 6,204,764 B1 | 3/2001 | Maloney |
| 6,220,451 B1 | 4/2001 | Hoffmann |
| 6,254,826 B1 | 7/2001 | Acosta |
| 6,265,225 B1 | 7/2001 | Otto |
| 6,274,374 B1 | 8/2001 | Astle |
| 6,299,567 B1 | 10/2001 | Forrest et al. |
| 6,325,129 B1 | 12/2001 | Wright |
| 6,335,166 B1 | 1/2002 | Ammann |
| 6,337,053 B1 | 1/2002 | Tajima |
| 6,355,488 B1 | 3/2002 | Rousseau |
| 6,358,472 B1 | 3/2002 | DeYoung |
| 6,361,744 B1 | 3/2002 | Levy |
| 6,368,561 B1 | 4/2002 | Rutishauser |
| 6,368,872 B1 | 4/2002 | Juranas |
| 6,374,989 B1 | 4/2002 | van Dyke, Jr. |
| 6,379,625 B1 | 4/2002 | Zuk, Jr. |
| 6,403,035 B1 | 6/2002 | Caratsch |
| 6,413,780 B1 | 7/2002 | Bach |
| 6,436,349 B1 | 8/2002 | Carey et al. |
| 6,440,368 B1 | 8/2002 | Cohen |
| 6,440,371 B1 | 8/2002 | Dumitrescu |
| 6,458,324 B1 | 10/2002 | Schinzel |
| 6,461,570 B2 | 10/2002 | Ishihara |
| 6,468,800 B1 | 10/2002 | Stylli |
| 6,472,218 B1 | 10/2002 | Stylli |
| 6,489,169 B1 | 12/2002 | Cohen |
| 6,498,037 B1 | 12/2002 | Carey et al. |
| 6,511,634 B1 | 1/2003 | Rittenhouse |
| 6,517,780 B1 | 2/2003 | Cortelazzo |
| 6,517,782 B1 | 2/2003 | Horner |
| 6,521,183 B1 | 2/2003 | Burri |
| 6,555,062 B1 | 4/2003 | Lewis et al. |
| 6,588,625 B2 | 7/2003 | Luoma, II et al. |
| 6,599,476 B1 | 7/2003 | Watson |
| 6,599,749 B1 | 7/2003 | Kodama et al. |
| 6,605,213 B1 | 8/2003 | Ammann |
| 6,673,595 B2 | 1/2004 | Barbera-Guillem |
| 6,677,857 B2 | 1/2004 | Bara et al. |
| 6,678,577 B1 | 1/2004 | Stylli |
| 6,685,884 B2 | 2/2004 | Stylli |
| 6,696,298 B2 | 2/2004 | Cook |
| 6,709,634 B1 | 3/2004 | Okada |
| 6,733,728 B1 | 5/2004 | Mimura |
| 6,746,648 B1 | 6/2004 | Mattila |
| 6,752,965 B2 | 6/2004 | Levy |
| 6,752,967 B2 | 6/2004 | Farina |
| 6,764,649 B2 | 7/2004 | Ammann |
| 6,776,964 B1 | 8/2004 | Wijnschenk |
| 6,790,412 B2 | 9/2004 | Willenbring |
| 6,790,413 B2 | 9/2004 | Ngo |
| 6,793,888 B2 | 9/2004 | Qureshi |
| 6,799,696 B2 | 10/2004 | Okada |
| 6,808,304 B2 | 10/2004 | Gebrian |
| 6,818,060 B2 | 11/2004 | Stewart |
| 6,827,902 B1 | 12/2004 | Kuriyama |
| 6,829,954 B2 | 12/2004 | Katagi |
| 6,843,357 B2 | 1/2005 | Bybee |
| 6,843,962 B2 | 1/2005 | Haslam |
| 6,846,456 B2 | 1/2005 | Acosta |
| 6,852,283 B2 | 2/2005 | Acosta |
| 6,878,343 B2 | 4/2005 | Sklar |
| 6,881,380 B1 | 4/2005 | Mootz |
| 6,890,485 B1 | 5/2005 | Stylli |
| 6,890,742 B2 | 5/2005 | Ammann |
| 6,893,611 B1 | 5/2005 | Cohen |
| 6,896,120 B2 | 5/2005 | Barry |
| 6,896,849 B2 | 5/2005 | Reed |
| 6,899,850 B2 | 5/2005 | Haywood |
| 6,939,513 B2 | 9/2005 | Berray |
| 6,948,389 B2 | 9/2005 | Brinker |
| 6,951,545 B2 | 10/2005 | Smith |
| 6,977,722 B2 | 12/2005 | Wohlstadter |
| 6,998,094 B2 | 2/2006 | Haslam |
| 6,999,847 B2 | 2/2006 | Barry et al. |
| 7,011,792 B2 | 3/2006 | Mimura |
| 7,028,831 B2 | 4/2006 | Veiner |
| 7,029,922 B2 | 4/2006 | Miller |
| 7,033,820 B2 | 4/2006 | Ammann |
| 7,067,323 B2 | 6/2006 | Veale et al. |
| 7,070,053 B1 | 7/2006 | Abrams |
| 7,091,864 B2 | 8/2006 | Veitch et al. |
| 7,112,303 B2 | 9/2006 | Itoh |
| 7,118,892 B2 | 10/2006 | Ammann |
| 7,125,722 B2 | 10/2006 | Safar |
| 7,135,145 B2 | 11/2006 | Ammann |
| 7,141,213 B1 | 11/2006 | Pang |
| 7,168,390 B2 | 1/2007 | Gudmundsson |
| 7,168,391 B2 | 1/2007 | Gudmundsson |
| 7,169,356 B2 | 1/2007 | Gebrian |
| 7,182,912 B2 | 2/2007 | Carey |
| 7,187,286 B2 | 3/2007 | Morris et al. |
| 7,199,712 B2 | 4/2007 | Tafas |
| 7,219,800 B2 | 5/2007 | Bülow |
| 7,220,385 B2 | 5/2007 | Blecka |
| 7,233,838 B2 | 6/2007 | Barry |
| 7,250,303 B2 | 7/2007 | Jakubowicz |
| 7,264,111 B2 | 9/2007 | Veiner |
| 7,267,795 B2 | 9/2007 | Ammann |
| 7,270,229 B2 | 9/2007 | Perazzo |
| 7,291,309 B2 | 11/2007 | Watson |
| 7,294,312 B2 | 11/2007 | Green |

(56) References Cited

U.S. PATENT DOCUMENTS

| | | |
|---|---|---|
| 7,299,981 B2 | 11/2007 | Hickle |
| 7,300,628 B2 | 11/2007 | Nogawa |
| 7,306,767 B2 | 12/2007 | Mathus |
| 7,309,469 B2 | 12/2007 | Anderson |
| 7,331,474 B2 | 2/2008 | Veiner |
| 7,338,635 B2 | 3/2008 | Miyake |
| 7,338,803 B2 | 3/2008 | Mizzer |
| 7,361,305 B2 | 4/2008 | Mimura |
| 7,380,654 B2 | 6/2008 | Barry |
| 7,382,258 B2 | 6/2008 | Oldham et al. |
| 7,384,600 B2 | 6/2008 | Burns |
| 7,396,509 B2 | 7/2008 | Burns |
| 7,400,983 B2 | 7/2008 | Feingold |
| 7,402,282 B2 | 7/2008 | LaCourt |
| 7,407,627 B1 | 8/2008 | Rosenberg |
| 7,411,508 B2 | 8/2008 | Harazin et al. |
| 7,448,487 B2 | 11/2008 | Koike |
| 7,458,483 B2 | 12/2008 | Luoma, II |
| 7,482,143 B2 | 1/2009 | Ammann |
| 7,488,453 B2 | 2/2009 | Takahashi |
| 7,491,364 B2 | 2/2009 | Mattila |
| 7,501,094 B2 | 3/2009 | Bysouth |
| 7,504,067 B2 | 3/2009 | Itoh |
| 7,510,683 B2 | 3/2009 | Itoh |
| 7,513,127 B2 | 4/2009 | Owen |
| 7,524,652 B2 | 4/2009 | Ammann |
| 7,526,968 B2 | 5/2009 | Lisec |
| 7,560,255 B2 | 7/2009 | Ammann |
| 7,560,256 B2 | 7/2009 | Ammann |
| 7,572,638 B2 | 8/2009 | Pressman |
| 7,625,748 B2 | 12/2009 | Ogura |
| 7,628,954 B2 | 12/2009 | Gomm |
| 7,638,337 B2 | 12/2009 | Ammann |
| 7,639,139 B2 | 12/2009 | Tafas |
| 7,641,855 B2 | 1/2010 | Farina |
| 7,662,339 B2 | 2/2010 | Mattila |
| 7,663,487 B2 | 2/2010 | Morris et al. |
| 7,666,602 B2 | 2/2010 | Ammann |
| 7,666,681 B2 | 2/2010 | Ammann |
| 7,667,603 B2 | 2/2010 | Bolander |
| 7,670,553 B2 | 3/2010 | Babson |
| 7,687,034 B2 | 3/2010 | Dumitrescu |
| 7,688,207 B2 | 3/2010 | Fritchie |
| 7,692,530 B2 | 4/2010 | Turner et al. |
| 7,700,043 B2 | 4/2010 | Mimura |
| 7,718,072 B2 | 5/2010 | Safar |
| 7,731,898 B2 | 6/2010 | Burkhardt |
| 7,754,149 B2 | 7/2010 | Sugiyama |
| 7,785,299 B2 | 8/2010 | Crawford |
| 7,790,108 B2 | 9/2010 | Müller |
| 7,818,132 B2 | 10/2010 | Pritchard |
| 7,842,504 B2 | 11/2010 | Devlin, Sr. |
| 7,846,384 B2 | 12/2010 | Watson |
| 7,850,912 B2 | 12/2010 | Favuzzi |
| 7,850,914 B2 | 12/2010 | Veiner et al. |
| 7,854,892 B2 | 12/2010 | Veiner et al. |
| 7,855,084 B2 | 12/2010 | Jakubowicz |
| 7,858,032 B2 | 12/2010 | Le Comte |
| 7,858,033 B2 | 12/2010 | Itoh |
| 7,866,464 B2 | 1/2011 | Miyatani et al. |
| 7,867,768 B2 | 1/2011 | Ryan |
| 7,875,245 B2 | 1/2011 | Favuzzi |
| 7,879,290 B2 | 2/2011 | Noda |
| 7,880,617 B2 | 2/2011 | Morris et al. |
| 7,901,624 B2 | 3/2011 | Hansen |
| 7,914,737 B2 | 3/2011 | Baumann |
| 7,922,986 B2 | 4/2011 | Byrnard |
| 7,931,861 B2 | 4/2011 | Kitagawa |
| 7,931,879 B2 | 4/2011 | D'Amore |
| 7,932,826 B2 | 4/2011 | Fritchie |
| 7,939,020 B2 | 5/2011 | Nogawa |
| 7,943,100 B2 | 5/2011 | Rousseau |
| 7,947,512 B2 | 5/2011 | Tajima |
| 7,975,852 B2 | 7/2011 | Charpentier |
| 7,976,794 B2 | 7/2011 | Trump |
| 7,985,375 B2 | 7/2011 | Edens |
| 7,998,409 B2 | 8/2011 | Veiner |
| 8,017,093 B2 | 9/2011 | Mattila |
| 8,017,094 B2 | 9/2011 | Meyer |
| 8,029,746 B2 | 10/2011 | Yu |
| 8,035,485 B2 | 10/2011 | Fritchie |
| 8,038,941 B2 | 10/2011 | Devlin |
| 8,012,419 B2 | 11/2011 | Eby |
| 8,049,623 B2 | 11/2011 | Morris et al. |
| 8,080,204 B2 | 12/2011 | Ryan |
| 8,211,301 B2 | 7/2012 | Safar |
| 8,252,232 B2 | 8/2012 | Neeper |
| 8,361,387 B2 | 1/2013 | Schacher |
| 8,361,396 B2 | 1/2013 | Parker |
| 8,435,738 B2 | 5/2013 | Holmes |
| 8,492,155 B2 | 7/2013 | Bunce |
| 2001/0019826 A1 | 9/2001 | Ammann |
| 2001/0041336 A1 | 11/2001 | Anderson et al. |
| 2002/0028489 A1 | 3/2002 | Ammann |
| 2002/0085959 A1 | 7/2002 | Carey |
| 2002/0098117 A1 | 7/2002 | Ammann |
| 2002/0127727 A1 | 9/2002 | Bach |
| 2002/0137194 A1 | 9/2002 | Ammann |
| 2002/0137197 A1 | 9/2002 | Ammann |
| 2002/0164807 A1 | 11/2002 | Itaya |
| 2003/0003591 A1 | 1/2003 | LaCourt et al. |
| 2003/0027206 A1 | 2/2003 | Ammann |
| 2003/0047418 A1 | 3/2003 | Okada |
| 2003/0054542 A1 | 3/2003 | Burns |
| 2003/0155321 A1 | 8/2003 | Bauer et al. |
| 2003/0194349 A1 | 10/2003 | Carey |
| 2003/0215357 A1 | 11/2003 | Leeker |
| 2003/0224524 A1 | 12/2003 | Arai et al. |
| 2004/0022682 A1 | 2/2004 | Itoh |
| 2004/0035816 A1 | 2/2004 | Okiyama |
| 2004/0042339 A1 | 3/2004 | Gebrian et al. |
| 2004/0094385 A1 | 5/2004 | Bybee |
| 2004/0096362 A1 | 5/2004 | Barry et al. |
| 2004/0115796 A1 | 6/2004 | Burns |
| 2004/0136869 A1 | 7/2004 | Itoh |
| 2004/0141882 A1 | 7/2004 | Mimura |
| 2004/0163931 A1 | 8/2004 | Barry et al. |
| 2004/0266015 A1 | 12/2004 | Favuzzi |
| 2005/0023109 A1 | 2/2005 | Barry |
| 2005/0042138 A1 | 2/2005 | Ueda |
| 2005/0084974 A1 | 4/2005 | Veale |
| 2005/0130198 A1 | 6/2005 | Ammann |
| 2005/0194237 A1 | 9/2005 | Veiner |
| 2005/0194333 A1 | 9/2005 | Veiner |
| 2005/0196320 A1 | 9/2005 | Veiner et al. |
| 2005/0233370 A1 | 10/2005 | Ammann |
| 2005/0239127 A1 | 10/2005 | Ammann |
| 2005/0258018 A1 | 11/2005 | Barry |
| 2005/0266489 A1 | 12/2005 | Ammann |
| 2005/0266570 A1 | 12/2005 | Carey |
| 2006/0003373 A1 | 1/2006 | Ammann |
| 2006/0013729 A1 | 1/2006 | Carey |
| 2006/0110288 A1 | 5/2006 | Mimura |
| 2006/0177346 A1 | 8/2006 | Veiner |
| 2006/0190185 A1 | 8/2006 | Ford et al. |
| 2006/0216199 A1 | 9/2006 | Koike |
| 2006/0258010 A1 | 11/2006 | Safar |
| 2006/0275906 A1 | 12/2006 | Devlin |
| 2007/0077172 A1 | 4/2007 | Sugiyama |
| 2007/0207056 A1 | 9/2007 | Veiner |
| 2007/0225857 A1 | 9/2007 | Barry |
| 2007/0243600 A1 | 10/2007 | Lair et al. |
| 2007/0255756 A1 | 11/2007 | Satomura et al. |
| 2008/0008624 A1 | 1/2008 | Veiner |
| 2008/0020467 A1 | 1/2008 | Barnes |
| 2008/0044260 A1 | 2/2008 | Miyatani |
| 2008/0063563 A1 | 3/2008 | Watari |
| 2008/0063573 A1 | 3/2008 | Ammann |
| 2008/0069730 A1 | 3/2008 | Itoh |
| 2008/0089818 A1 | 4/2008 | Ammann |
| 2008/0096214 A1 | 4/2008 | Ammann |
| 2008/0102527 A1 | 5/2008 | Ammann |
| 2008/0181817 A1 | 7/2008 | Mimura |
| 2008/0190735 A1 | 8/2008 | Luoma |

(56) References Cited

U.S. PATENT DOCUMENTS

| | | |
|---|---|---|
| 2008/0212400 A1 | 9/2008 | Ammann |
| 2008/0226498 A1 | 9/2008 | Stylli |
| 2008/0226509 A1 | 9/2008 | Sattler |
| 2008/0241837 A1 | 10/2008 | Ammann |
| 2008/0268528 A1 | 10/2008 | Ammann |
| 2008/0299007 A1 | 12/2008 | Noguchi |
| 2009/0029352 A1 | 1/2009 | Ammann |
| 2009/0029871 A1 | 1/2009 | Ammann |
| 2009/0029877 A1 | 1/2009 | Ammann |
| 2009/0058617 A1 | 3/2009 | Wu |
| 2009/0074616 A1 | 3/2009 | Sento |
| 2009/0130749 A1 | 5/2009 | Ammann |
| 2009/0134978 A1 | 5/2009 | Imai |
| 2009/0160654 A1 | 6/2009 | Yang |
| 2009/0162247 A1 | 6/2009 | Tokieda |
| 2009/0325274 A1 | 12/2009 | Hamada |
| 2010/0001854 A1 | 1/2010 | Kojima |
| 2010/0001876 A1 | 1/2010 | Sasaki |
| 2010/0007501 A1 | 1/2010 | Yang |
| 2010/0013595 A1 | 1/2010 | Torre-Bueno |
| 2010/0021993 A1 | 1/2010 | Wang |
| 2010/0028124 A1 | 2/2010 | Lackner |
| 2010/0034701 A1 | 2/2010 | Pedrazzini |
| 2010/0075430 A1 | 3/2010 | Hofstadler |
| 2010/0112703 A1 | 3/2010 | Farrar |
| 2010/0093097 A1 | 4/2010 | Kawamura |
| 2010/0097231 A1 | 4/2010 | Elsenhans |
| 2010/0122586 A1 | 5/2010 | Misu |
| 2010/0124518 A1 | 5/2010 | Koike |
| 2010/0166605 A1 | 7/2010 | Hamada |
| 2010/0166615 A1 | 7/2010 | Mattila |
| 2010/0188244 A1 | 7/2010 | Sattler et al. |
| 2010/0191382 A1 | 7/2010 | Samuhel |
| 2010/0248213 A1 | 9/2010 | Feiglin |
| 2010/0282003 A1 | 11/2010 | Hamada |
| 2010/0300831 A1 | 12/2010 | Pedrazzini |
| 2010/0314216 A1 | 12/2010 | Lanfranchi |
| 2011/0001609 A1 | 1/2011 | Oldham et al. |
| 2011/0027150 A1 | 2/2011 | Tuffet |
| 2011/0064543 A1 | 3/2011 | Nuotio |
| 2011/0073438 A1 | 3/2011 | Takai |
| 2011/0076193 A1 | 3/2011 | Kitagawa |
| 2011/0076194 A1 | 3/2011 | Kitagawa |
| 2011/0076780 A1 | 3/2011 | Yamato |
| 2011/0090066 A1 | 4/2011 | Yamaguchi et al. |
| 2011/0091364 A1 | 4/2011 | Voit |
| 2011/0095864 A1 | 4/2011 | Trueeb et al. |
| 2011/0123416 A1 | 5/2011 | Giraud |
| 2011/0143947 A1 | 6/2011 | Chamberlin |
| 2011/0158850 A1 | 6/2011 | Pedrazzini |
| 2011/0189051 A1 | 8/2011 | Gelin |
| 2011/0197661 A1 | 8/2011 | Hansjürgen |
| 2011/0200500 A1 | 8/2011 | Feilders |
| 2011/0229374 A1 | 9/2011 | Tokunaga |
| 2011/0232372 A1 | 9/2011 | Tokunaga |
| 2011/0236259 A1 | 9/2011 | Mototsu |
| 2011/0243792 A1 | 10/2011 | Tatsutani |
| 2011/0256022 A1 | 10/2011 | Akutsu |
| 2011/0276087 A1 | 11/2011 | Breidenthal et al. |
| 2012/0028847 A1 | 2/2012 | Indermuhle |
| 2012/0308425 A1 | 12/2012 | Morishita |
| 2012/0308435 A1 | 12/2012 | Fritchie |

FOREIGN PATENT DOCUMENTS

| | | |
|---|---|---|
| CA | 2502656 | 2/2004 |
| CA | 2693321 | 2/2004 |
| DE | 102007031117 | 1/2008 |
| DE | 102007012524 | 9/2008 |
| EP | 0036566 | 9/1984 |
| EP | 0564970 | 10/1993 |
| EP | 0577343 | 1/1994 |
| EP | 0622305 | 11/1994 |
| EP | 0631816 | 1/1995 |
| EP | 0651254 | 5/1995 |
| EP | 0467284 | 6/1995 |
| EP | 0692308 | 1/1996 |
| EP | 0694334 | 1/1996 |
| EP | 0866335 | 9/1998 |
| EP | 0734963 | 11/1998 |
| EP | 0884104 | 12/1998 |
| EP | 0909584 | 4/1999 |
| EP | 0920915 | 6/1999 |
| EP | 0738541 | 1/2002 |
| EP | 0757253 | 4/2003 |
| EP | 1122181 | 5/2003 |
| EP | 1546009 | 2/2004 |
| EP | 1546736 | 2/2004 |
| EP | 0968766 | 9/2004 |
| EP | 1216754 | 11/2004 |
| EP | 0977037 | 8/2005 |
| EP | 1566216 | 8/2005 |
| EP | 1424291 | 3/2006 |
| EP | 1655071 | 5/2006 |
| EP | 1452869 | 11/2006 |
| EP | 1739406 | 1/2007 |
| EP | 1741488 | 1/2007 |
| EP | 1231472 | 1/2008 |
| EP | 1550498 | 7/2008 |
| EP | 1767949 | 10/2008 |
| EP | 1832880 | 10/2009 |
| EP | 1546680 | 3/2011 |
| EP | 2074431 | 4/2011 |
| GB | 2354841 | 4/2001 |
| JP | 8026461 | 1/1996 |
| JP | 09166599 | 6/1997 |
| JP | 09304397 | 11/1997 |
| JP | 2000019182 | 1/2000 |
| JP | 2000162215 | 6/2000 |
| JP | 2001253530 | 9/2001 |
| JP | 2003083987 | 3/2003 |
| JP | 2007527011 | 9/2007 |
| JP | 2008073653 | 4/2008 |
| JP | 2010085125 | 4/2010 |
| WO | WO9409352 | 4/1994 |
| WO | WO9511083 | 4/1995 |
| WO | WO9621851 | 7/1996 |
| WO | WO9705492 | 2/1997 |
| WO | WO9716734 | 5/1997 |
| WO | WO9803264 | 1/1998 |
| WO | WO9809579 | 3/1998 |
| WO | WO9821594 | 5/1998 |
| WO | WO9858262 | 12/1998 |
| WO | WO9945360 | 9/1999 |
| WO | WO9951718 | 10/1999 |
| WO | WO9952634 | 10/1999 |
| WO | WO0029114 | 5/2000 |
| WO | WO0117682 | 3/2001 |
| WO | WO0245648 | 6/2002 |
| WO | WO03000420 | 1/2003 |
| WO | WO03020427 | 3/2003 |
| WO | WO2004013615 | 2/2004 |
| WO | WO2004013639 | 2/2004 |
| WO | WO2004013709 | 2/2004 |
| WO | WO2004013710 | 2/2004 |
| WO | WO2006021648 | 3/2006 |
| WO | WO2007134066 | 11/2007 |
| WO | WO2008113352 | 9/2008 |
| WO | WO2009012808 | 1/2009 |
| WO | WO2009024560 | 2/2009 |
| WO | WO2009115760 | 9/2009 |
| WO | WO2009144381 | 12/2009 |
| WO | WO2009149324 | 12/2009 |
| WO | WO2010132885 | 11/2010 |
| WO | WO2011139888 | 11/2011 |
| WO | WO2012057548 | 5/2012 |

# LIGHT-BLOCKING SYSTEM FOR A DIAGNOSTIC ANALYZER

CROSS-REFERENCE TO RELATED APPLICATIONS

This application is a divisional of U.S. non-provisional application Ser. No. 14/214,190, now U.S. Pat. No. 9,513,303, filed on Mar. 14, 2014 and claims the benefit of priority to U.S. provisional application No. 61/790,480, filed on Mar. 15, 2013, both of which are incorporated by reference in their entireties.

FIELD OF THE DISCLOSURE

This disclosure relates to a selectively activated light-blocking system for a diagnostic analyzer.

BACKGROUND

Diagnostic analyzers for testing samples typically utilize a moving carousel containing a processing path. The moving carousel holds reaction vessels which contain samples to be tested by the diagnostic analyzer. Pipetting devices transfer reagents into the reaction vessels to be mixed with the samples. In order to diagnostically test the samples containing the reagents, the pipetting devices transfer the samples from the moving carousel to a testing device which is off-track from the moving carousel. This increases cost, takes up space, and decreases throughput.

A diagnostic analyzer is needed to overcome one or more of the issues of one or more of the existing diagnostic analyzers.

SUMMARY

In one embodiment, a diagnostic analyzer is disclosed. The diagnostic analyzer includes a track, at least one light-blocking member, a motor, and an optical testing device. The track is for moving a reaction vessel held by the track. The at least one light-blocking member is disposed adjacent to the track. The at least one light-blocking member is configured to move from a first position apart from the track to a second position closer to the track. When the at least one light-blocking member is disposed in the first position a sample contained within the reaction vessel held by the track is exposed to light. When the at least one light-blocking member is disposed in the second position the sample contained within the reaction vessel held by the track is blocked from exposure to the light by the at least one light-blocking member. The motor is for moving the at least one light-blocking member between the first and the second positions. The optical testing device is disposed adjacent to the track for optically testing the sample contained within the reaction vessel held by the track when the at least one light-blocking member is disposed in the second position blocking the sample from exposure to the light.

In another embodiment, a diagnostic analyzer is disclosed. The diagnostic analyzer includes a track, two opposed sets of light-blocking members, at least one motor, a plurality of linkage members, and at least one optical testing device. The track includes a plurality of lanes for holding reaction vessels containing samples. The two opposed sets of light-blocking members are disposed apart on opposite sides of the track. Each of the two opposed sets of light-blocking members are adjacent to a different one of the plurality of lanes. Each of the two opposed sets of light-blocking members include a first light-blocking member and a second light-blocking member. The plurality of linkage members connect the two opposed sets of light-blocking members to the at least one motor. The at least one motor is configured to move the two opposed sets of light-blocking members between a first position and a second position. In the first position, the two opposed sets of light-blocking members allow light exposure to the samples in the reaction vessels held in the plurality of lanes. In the second position, the two opposed sets of light-blocking members block light exposure to the samples in the reaction vessels held in the plurality of lanes.

In still another embodiment, a method of diagnostically testing a sample is disclosed. In one step, a track holding a reaction vessel, which contains a sample, is moved so that the reaction vessel is disposed adjacent to at least one light-blocking member in a first position disposed apart from the track allowing the sample to be exposed to light. In another step, the at least one light-blocking member is moved from the first position to a second position closer to the track to dispose the reaction vessel held by the track within at least a portion of the at least one light-blocking member to block the sample contained within the reaction vessel from exposure to the light. In an additional step, the sample is optically tested while the at least one light-blocking member is disposed in the second position.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
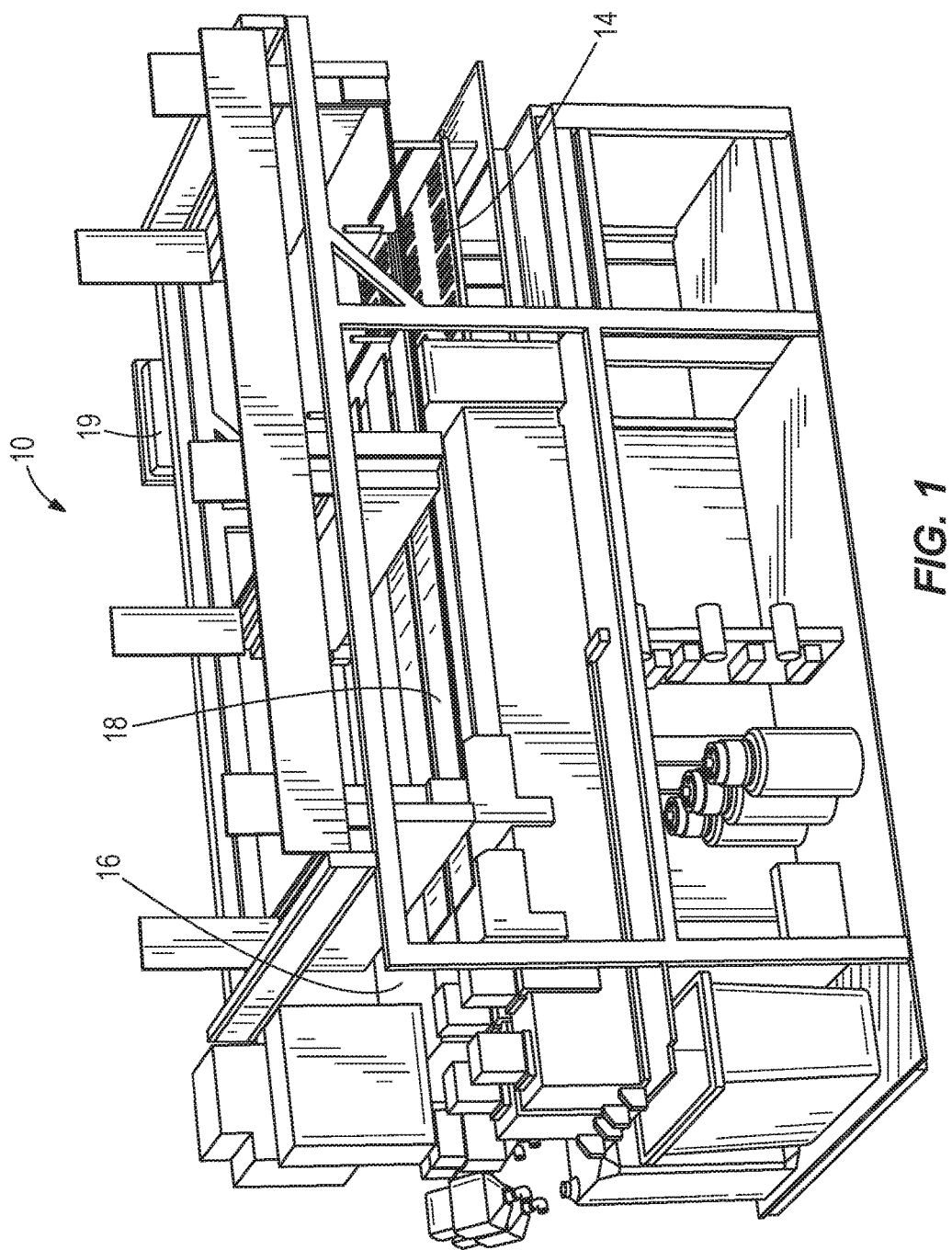
FIG. 1 illustrates a perspective view of one embodiment of a diagnostic analyzer system.
Figure 2:
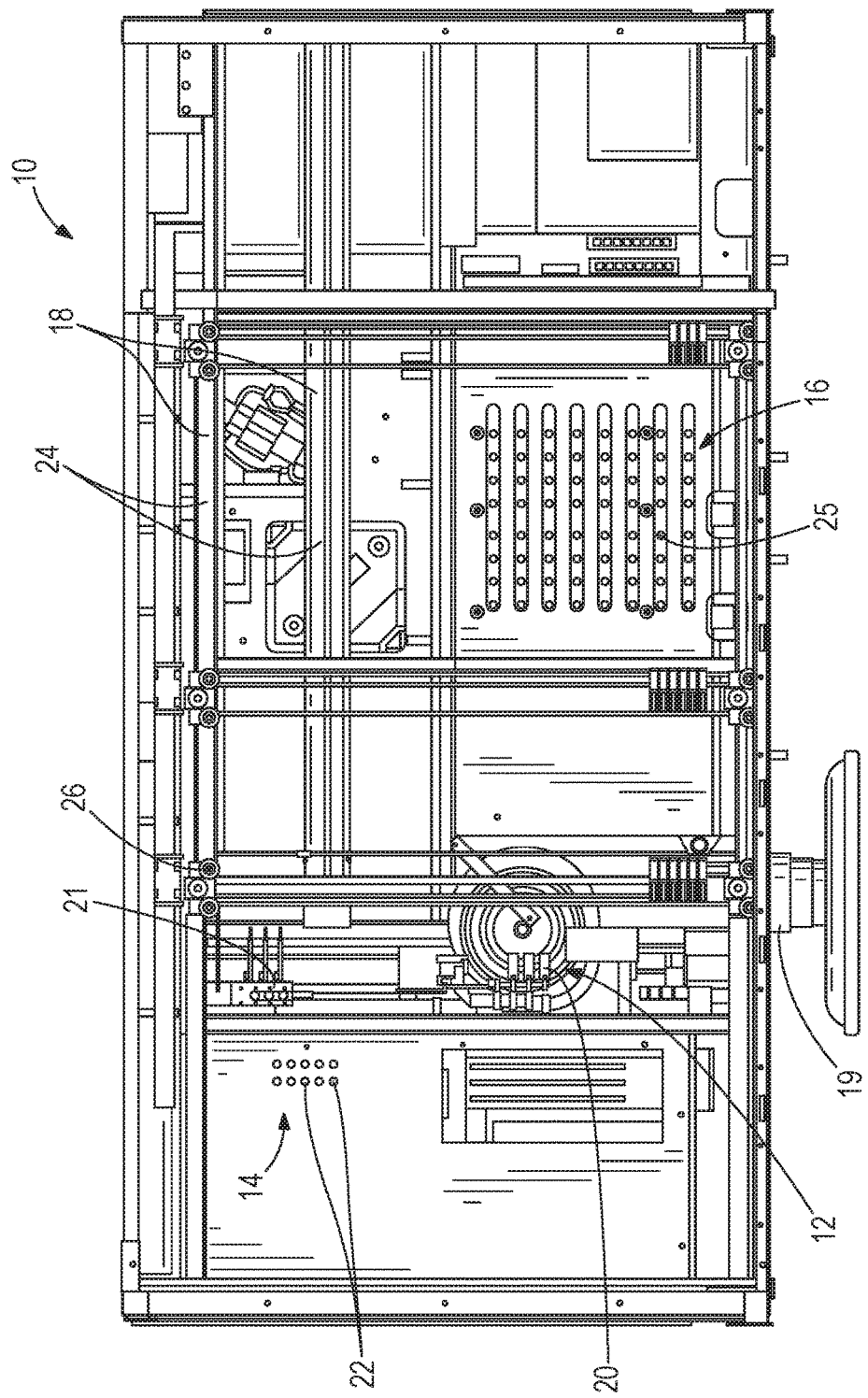
FIG. 2 illustrates a top view of one embodiment of a diagnostic analyzer system.

FIGS. 1 and 2 respectively illustrate a perspective view and a top view of one embodiment of a diagnostic analyzer system 10. As shown collectively in FIGS. 1 and 2, the diagnostic analyzer system 10 comprises a reaction vessel loading zone 12, a sample storage zone 14, a reagent storage zone 16, a testing zone 18, and one or more processors 19. The one or more processors 19 may control the actions of the diagnostic analyzer system 10. The reaction vessel loading zone 12 comprises a zone which supplies reaction vessels 20 to the testing zone 18 preferably using a robot 21. The sample storage zone 14 comprises a zone which supplies samples 22 to the testing zone 18 for testing. The samples 22 comprise blood samples. The blood samples may be taken from a mammal, a human, an animal, or any type of living creature. In other embodiments, the samples 22 may vary. The reagent storage zone 16 comprises a zone which supplies reagents 25 to the testing zone 18. The testing zone 18 comprises a zone which conducts testing on the samples 22 to determine a measurement, a property, a trait, or a condition of the samples 22. The testing zone 18 comprises two linear tracks 24. In other embodiments, the testing zone 18 may comprise any number of linear moving tracks 24. The moving linear tracks 24 are made of stainless steel. The moving linear tracks 24 and the entire assemblies are conductive to eliminate a build-up of static electricity. The moving linear tracks 24 are identical. In other embodiments, the moving linear tracks 24 may vary. Motor 26 provides power for moving the linear tracks 24. In other embodiments, any number of motors 26 may be used to provide power for moving the linear tracks 24.

Figure 3:
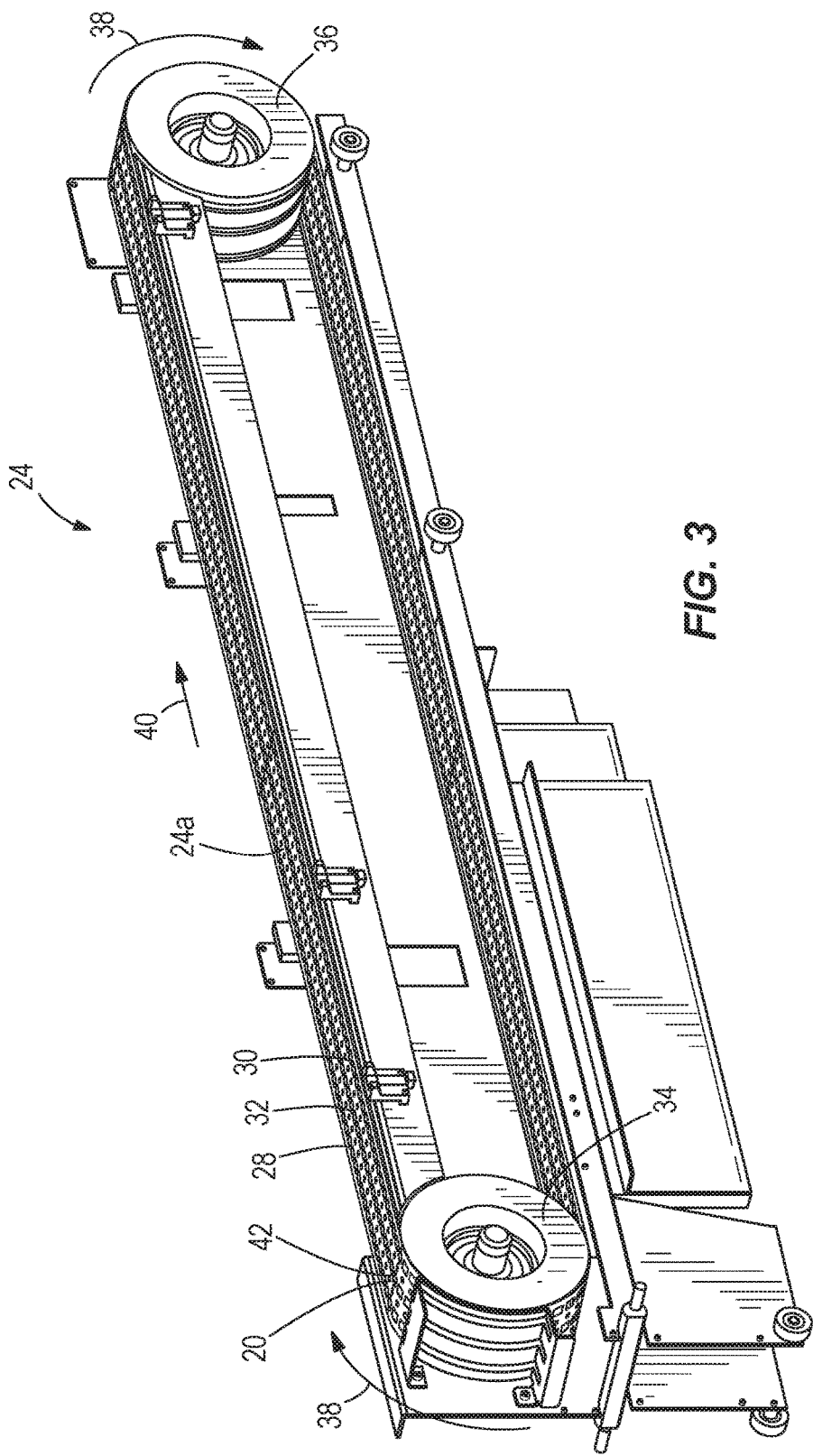
FIG. 3 illustrates a perspective view of one linear track of FIGS. 1 and 2 removed from the diagnostic analyzer system.

FIG. 3 illustrates a perspective view of one of the linear tracks 24 of FIGS. 1 and 2 removed from the diagnostic analyzer system 10. The linear track 24 comprises two outer processing lanes 28 and 30, and a pre-treatment lane 32 which is disposed between and parallel to the two outer processing lanes 28 and 30. As more thoroughly discussed below, the outer processing lanes 28 and 30 are used to conduct diagnostic tests on samples. In other embodiments, the linear track 24 may comprise any number of processing and pre-treatment lanes in varied configurations. The linear track 24 is disposed around pulleys 34 and 36 forming a continuous linear track 24. The motor 26 of FIG. 2 supplies power to one or more of the pulleys 34 and 36 of FIG. 3 in order to rotate the pulleys 34 and 36 in the clockwise direction 38. The rotation of the pulleys 34 and 36 causes the attached linear track 24 to rotate with and around the pulleys 34 and 36 in the clockwise direction 38 thereby moving the outer processing lanes 28 and 30 and the pre-treatment lane 32 of the linear track 24 identically. As a top portion 24a of the linear track 24 moves in linear direction 40 due to the rotation of the pulleys 34 and 36, the reaction vessels 20 held in place within a plurality of slots 42 of the linear track 24 also move in linear direction 40. The plurality of slots 42 are precision laser-cut slots of the linear track 24.

Figure 4:
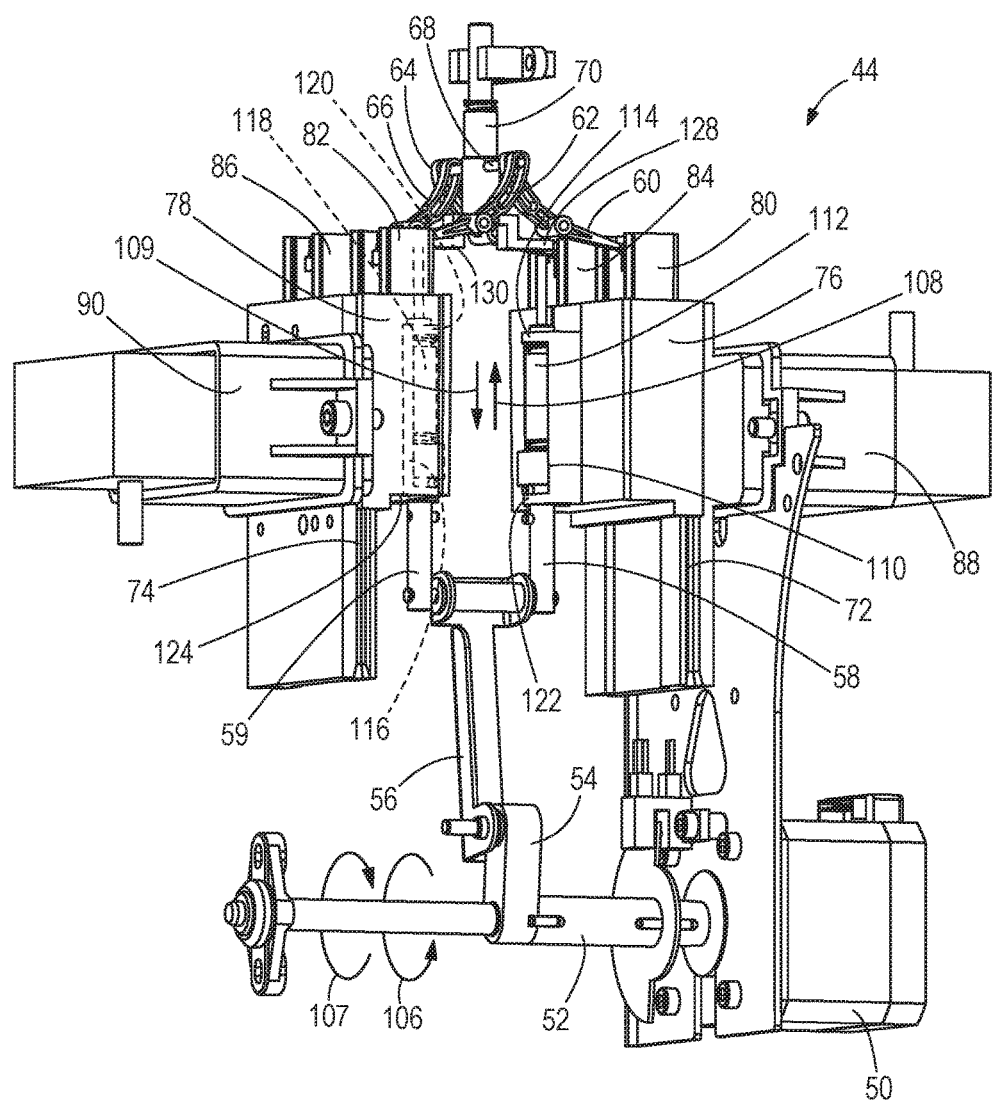
FIG. 4 illustrates a perspective view of a testing device, disposed in a closed position, which is used to test samples in a testing zone of the diagnostic analyzer of FIG. 1.
Figure 5:
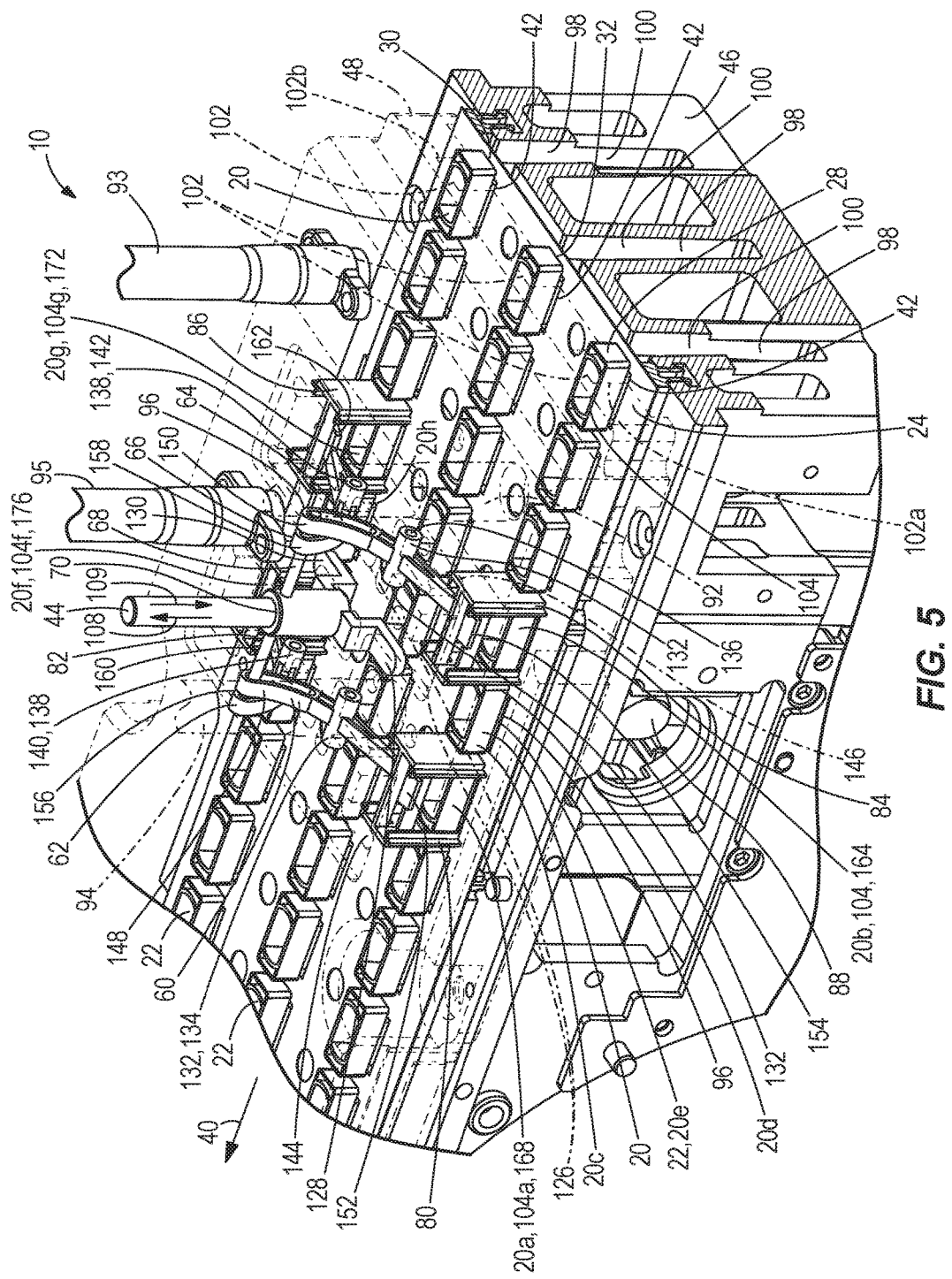
FIG. 5 illustrates a cross-section view through a moving track of the diagnostic analyzer of FIG. 1 with the testing device of FIG. 4 disposed in the closed position relative to the moving track.

FIG. 4 illustrates a perspective view of a testing device 44, disposed in a closed position, which is used to test samples 22 in the testing zone 18 of the diagnostic analyzer 10 of FIG. 1. FIG. 5 illustrates a cross-section view through a moving track 24 of the diagnostic analyzer 10 of FIG. 1 with the testing device 44 of FIG. 4 disposed in the closed position relative to the moving track 24. The closed position is also referred to herein as the second position. The testing device 44 of the diagnostic analyzer 10 may be used to diagnostically analyze the samples 22 contained within the reaction vessels 20 held within the slots 42 of the processing lanes 28 and 30 of the moving track 24 in order to determine a trait, characteristic, property, or condition of the samples 22. The slots 42 within the pre-treatment lane 32 of the moving track 24 also contain reaction vessels 20 but the testing device 44 of the diagnostic analyzer 10 is not used to diagnostically analyze samples in the reaction vessels 20 held by the pre-treatment lane 32.

As shown collectively in FIGS. 4 and 5, the diagnostic analyzer 10 comprises in-part: the moving track 24; bottom housing 46; top housing 48; motor 50; shaft 52; linkage members 54, 56, 58, 59, 60, 62, 64, 66, 68, and 70; frame members 72 and 74; first light-blocking members 76 and 78; second light-blocking members 80, 82, 84, and 86; optical testing devices 88 and 90; pre-trigger devices 92 and 93; and trigger devices 94 and 95.

The processor 19 of FIG. 2 causes the motor 26 of FIG. 2 to intermittently move the moving track 24 of FIG. 5 in direction 40 such that the reaction vessels 20 held by the slots 42 of the processing lanes 28 and 30 are each disposed at location 96 for a pre-determined time delay. The optical testing devices 88 and 90 are located at location 96 for diagnostically testing the samples 22 contained in the reaction vessels 20 held by the slots 42 of the processing lanes 28 and 30.

The slots 42 of the processing lanes 28 and 30 and the slots 42 of the pre-treatment lane 32 are each aligned with separate respective elongated channels 98 of the bottom housing 46 which is disposed below the moving track 24. The separate respective elongated channels 98 of the bottom housing 46 are sized to hold bottom portions 100 of the reaction vessels 20 which are extended through the slots 42 in the processing lanes 28 and 30 and through the slots 42 in the pre-treatment lane 32. Similarly, the slots 42 of the processing lanes 28 and 30 and the slots 42 of the pre-treatment lane 32 are each aligned with separate respective elongated channels 102 of the top housing 48 which is disposed above the moving track 24. The separate respective elongated channels 102 of the top housing 48 are sized to hold top portions 104 of the reaction vessels 20 which are extended through the slots 42 in the processing lanes 28 and 30 and through the slots 42 in the pre-treatment lane 32. In such manner, when the moving track 24 advances in direction 40 the reaction vessels 20 held in the slots 42 of the track 24 are configured to move through the elongated channels 98 and 102 of the bottom and top housings 46 and 48 in direction 40.

As shown collectively in FIG. 4, the motor 50 is connected to shaft 52 for rotating the shaft one-hundred-eighty degrees (180 degrees) back and forth in directions 106 and 107. Shaft 52 is fixedly attached to linkage member 54 such that linkage member 54 rotates with the shaft 52. Linkage member 54 is pivotally attached to linkage member 56 such that movement of linkage member 54 causes linkage member 56 to pivot. Linkage member 56 is pivotally attached to linkage member 58 such that pivoting of linkage member 56 causes linkage member 58 to slide up in direction 108 or down in direction 109 within compartment 110 of the first light-blocking member 76. When linkage member 58 is moved upwardly in direction 108 within compartment 110 a portion 112 of the linkage member 58 abuts against a top ledge 114 of the compartment 110 of the first light-blocking member 76 causing the first light-blocking member 76 to move upwardly in direction 108 into the closed position while sliding along frame member 72 to which it is moveably attached.

Linkage member 56 is also pivotally attached to linkage member 59 such that pivoting of linkage member 56 also causes linkage member 59 to slide up in direction 108 or down in direction 109 within compartment 116 of the first light-blocking member 78. When linkage member 59 is moved upwardly in direction 108 within compartment 116 a portion 118 of the linkage member 59 abuts against a top ledge 120 of the compartment 116 of the first light-blocking member 78 causing the first light-blocking member 78 to move upwardly in direction 108 while sliding along frame member 74 to which it is moveably attached.

Figure 6:
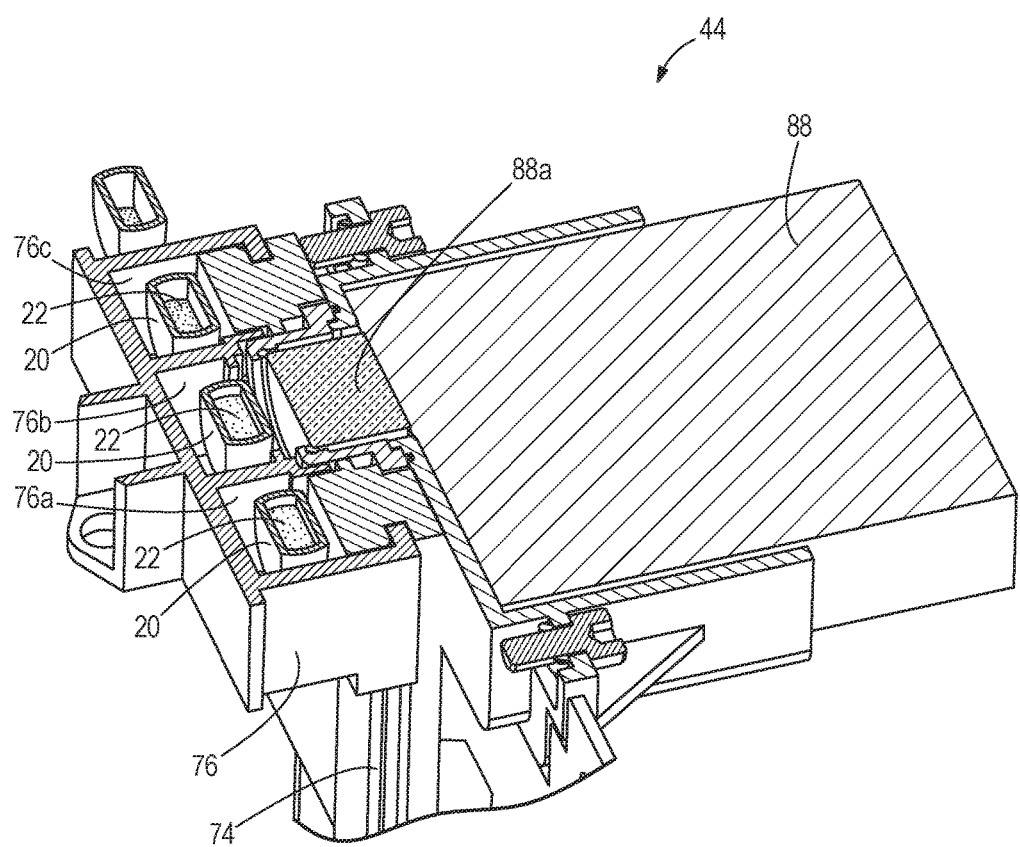
FIG. 6 illustrates a cross-section view through a first light-blocking member of the testing device of FIG. 4 while the first light-blocking member is disposed in the closed position.

FIG. 6 illustrates a cross-section view through the first light-blocking member 76 of the testing device 44 of FIG. 4 while the first light-blocking member 76 is disposed in the closed position. As shown, the first light-blocking member 76 comprises a plurality of inner compartments 76a, 76b, and 76c having open top ends. When the first light-blocking member 76 is disposed in the closed position the plurality of inner compartments 76a, 76b, and 76c of the first light-blocking member 76 each enclose a separate respective reaction vessel 20 each holding a separate respective sample 22. While in this closed position, the first light-blocking member 76 is disposed within the elongated channel 98a (See FIG. 5) of the bottom housing 46 and abuts against a bottom of the track 24 completing enclosing the reaction vessels 20 within the compartments 76a, 76b, and 76c of the first light-blocking member 76. While in this closed position, the frame member 74 and an optical reader 88a of the optical testing device 88 form walls of the inner compartments 76a, 76b, and 76c. The first light-blocking member 78 of FIG. 4 is a mirror image of the first light-blocking member 76 and functions the same way to enclose reaction vessels 20 disposed on the other side of the testing device 44 when the first light-blocking member 78 is disposed in the closed position.

When linkage member 58 of FIG. 4 is moved downwardly in direction 109 within compartment 110 the portion 112 of the linkage member 58 abuts against a bottom ledge 122 of the compartment 110 of the first light-blocking member 76 causing the first light-blocking member 76 to move downwardly in direction 109 while sliding along frame member 72 to which it is moveably attached. When linkage member 59 is moved downwardly in direction 109 within compartment 116 the portion 118 of the linkage member 59 abuts against a bottom ledge 124 of the compartment 116 of the first light-blocking member 78 causing the first light-blocking member 78 to move downwardly in direction 109 while sliding along frame member 74 to which it is moveably attached.

When linkage members 58 and 59 are moved upwardly in direction 108 they extend through holes 126 (see FIG. 5) in the track 24 and make contact with tabs 128 and 130 of linkage member 70 causing linkage member 70 to move upward in direction 108 through hole 132 in the top housing 48. This upward movement of the linkage member 70 in direction 108 causes linkage member 68, which is disposed above the top housing 48 and fixedly attached to linkage member 70, to also move upwardly in direction 108. Linkage members 60, 62, 64, and 66 are pivotally attached to linkage member 68. One or more pins 132 extend in fixed attachment within the top housing 48 through channels 134 and 136 in linkage members 60 and 64. Another one or more pins 138 extends in fixed attachment within the top housing 48 through channels 140 and 142 in linkage members 62 and 66. Linkage members 60, 62, 64, and 66 extend through holes 144 and 146 in the top housing 48.

Upward movement of the linkage member 68 in direction 108 (due to the linked movement previously described) causes attached linkage members 60 and 64 to pivot relative to the linkage member 68 and relative to the fixed pin 132. This causes, in a teeter-totter movement, top portions 148 and 150 of linkage members 60 and 64 to move upwardly in direction 108 and causes bottom portions 152 and 154 of linkage members 60 and 64 to move downwardly in direction 109. This downward movement of the bottom portions 152 and 154 of linkage members 60 and 64 in direction 109 causes the respectively attached second light-blocking members 80 and 84 to also travel downward in direction 109 in order to abut against the track 24 in the closed position.

The upward movement of the linkage member 68 in direction 108 also causes attached linkage members 62 and 66 to pivot relative to the linkage member 68 and relative to the fixed pin 138. This causes, in a teeter-totter movement, top portions 156 and 158 of linkage members 62 and 66 to move upwardly in direction 108 and also causes bottom portions 160 and 162 of linkage members 62 and 66 to move downwardly in direction 109. This downward movement of the bottom portions 160 and 162 of linkage members 62 and 66 in direction 109 causes the respectively attached second light-blocking members 82 and 86 to also travel downward in direction 109 in order to abut against the track 24 in the closed position.

The second light-blocking members 80 and 84 comprise shutters. In the closed position the second light-blocking members 80 and 84 are disposed in the elongated channel 102a of the top housing 48 abutted against the track 24 at least partially surrounding reaction vessels 20a and 20b which are disposed on opposite sides 20c and 20d of reaction vessel 20e. When in the closed position, the second light-blocking members 80 and 84 enclose the reaction vessel 20e between the second light-blocking members 80 and 84 within the elongated channel 102a of the top housing 48. In this closed position the second light-blocking member 84 blocks light 164 emanating from a top portion 104b of reaction vessel 20b from reaching the reaction vessel 20e. The light 164 was created due to the pre-trigger device 92 having injected a pre-trigger solution into reaction vessel 20b at location 165.

In this closed position the second light-blocking member 80 blocks light 168 emanating from a top portion 104a of reaction vessel 20a from reaching the reaction vessel 20e. The light 168 results due to the trigger device 94 injecting a trigger solution into reaction vessel 20b at location 96 which creates the light 168. While in this closed position, with light 164 and 168 being blocked above the track 24 by the second light-blocking members 84 and 80, the optical testing device 88 is used to diagnostically test the sample 22 within reaction vessel 20e. The optical testing device 88 may comprise a chemiluminescence optical testing device. In other embodiments, the optical testing device 88 may vary.

The second light-blocking members 82 and 86 also comprise shutters. In the closed position the second light-blocking members 82 and 86 are disposed in the elongated channel 102b of the top housing 48 abutted against the track 24 at least partially surrounding reaction vessels 20f and 20g which are disposed on opposite sides of reaction vessel 20h. When in the closed position, the second light-blocking members 82 and 86 enclose the reaction vessel 20h between the second light-blocking members 82 and 86 within the elongated channel 102b of the top housing 48. In this closed position the second light-blocking member 86 blocks light 172 emanating from a top portion 104g of reaction vessel 20g from reaching the vessel 20h. The light 172 results due to the pre-trigger device 93 having injected a pre-trigger solution into reaction vessel 20g at location 165.

In this closed position the second light-blocking member 82 blocks light 176 emanating from a top portion 104f of reaction vessel 20f from reaching the reaction vessel 20h. The light 176 results due to the trigger device 95 injecting a trigger solution into reaction vessel 20f at location 96. While in this closed position, with light 172 and 176 being blocked above the track 24 by the second light-blocking members 86 and 82, the optical testing device 90 (see FIG. 4) is used to diagnostically test the sample 22 within reaction vessel 20h. The optical testing device 90 may comprise a chemiluminescence optical testing device. In other embodiments, the optical testing device 90 may vary.

Figure 7:
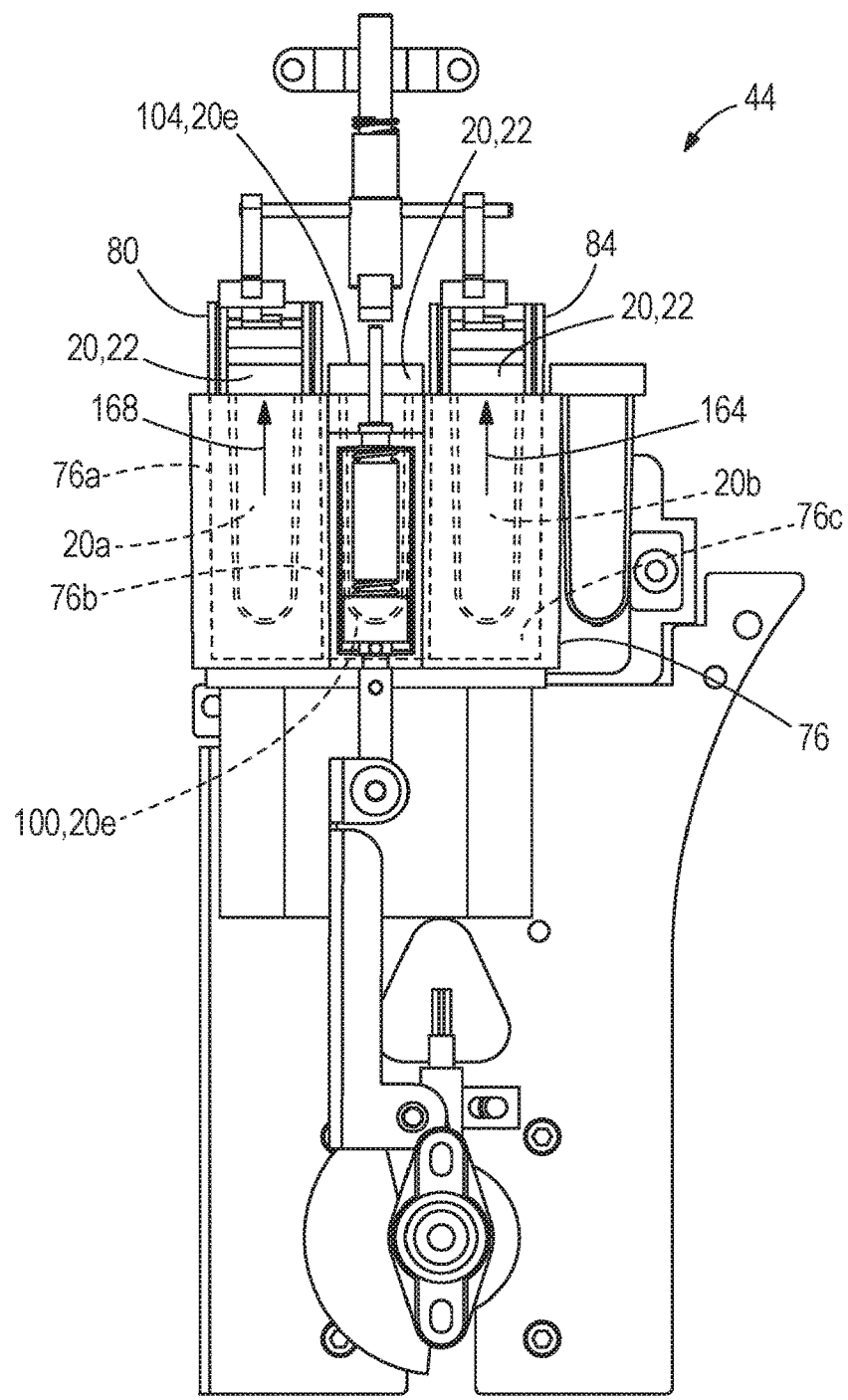
FIG. 7 illustrates a cross-section view through a first light-blocking member and second light-blocking members of the testing device of FIG. 4 while the first light-blocking member and the second light-blocking members are disposed in the closed position.

FIG. 7 illustrates a cross-section view through the first light-blocking member 76 and the second light-blocking members 80 and 84 of the testing device 44 of FIG. 4 while the first light-blocking member 76 and the second light-blocking members 80 and 84 are disposed in the closed position. As shown, in this closed position the plurality of inner compartments 76a, 76b, and 76c of the first light-blocking member 76 each completely enclose a separate respective reaction vessel 20 each holding a separate respective sample 22. While in this closed position, the first light-blocking member 76 is disposed against a bottom of the track 24 (see FIG. 5) completing enclosing the reaction vessels 20 within the inner compartments 76a, 76b, and 76c of the first light-blocking member 76. In this closed position, as shown in FIG. 6, the frame member 74 and the optical reader 88a of the optical testing device 88 form walls of the inner compartments 76a, 76b, and 76c. As shown in FIG. 7, when the first light-blocking member 76 is disposed in this closed position the light 164 emanating from the reaction vessel 20b is blocked from reaching the bottom portion 100 of reaction vessel 20e below the track 24 (see FIG. 5) due to the separated inner compartments 76c and 76b of the first light-blocking member 76. Similarly, while the first light-blocking member 76 is disposed in this closed position the light 168 emanating from the reaction vessel 20a is blocked from reaching the bottom portion 100 of reaction vessel 20e below the track 24 (see FIG. 5) due to the separated inner compartments 76a and 76b of the first light-blocking member 76. The first light-blocking member 78 (see FIG. 4) is a mirror image of the first light-blocking member 76 and functions the same way to block light from the reaction vessels disposed on the other side of the testing device 44 when disposed in the closed position.

Additionally, the second light-blocking members 80 and 84 in the closed position enclose the reaction vessel 20e between the second light-blocking members 80 and 84 within the elongated channel 102a (see FIG. 5) of the top housing 48 (see FIG. 5) thereby blocking the respective light 168 and 164 emanating from the reaction vessels 20a and 20b from reaching the top portion 104 of the reaction vessel 20e above the track 24 (see FIG. 5). The second light-blocking members 82 and 86 (see FIG. 5) are mirror images of the second light-blocking members 80 and 84 and function the same way to block light from the reaction vessels disposed on the other side of the testing device 44 when disposed in the closed position.

In such manner, as shown collectively in FIGS. 4, 5, and 7, when the first light-blocking members 76 and 78 and the second light blocking members 80, 82, 84, and 86 are disposed in the closed positions the samples 22 contained in the reaction vessels 20e and 20h being tested by the optical testing devices 88 and 90 are blocked from exposure to light both above and below the track 24. This is important as the exposure of the samples 22 contained in the reaction vessels 20e and 20h to light during testing can reduce the accuracy of the diagnostic testing of the samples.

Figure 8:
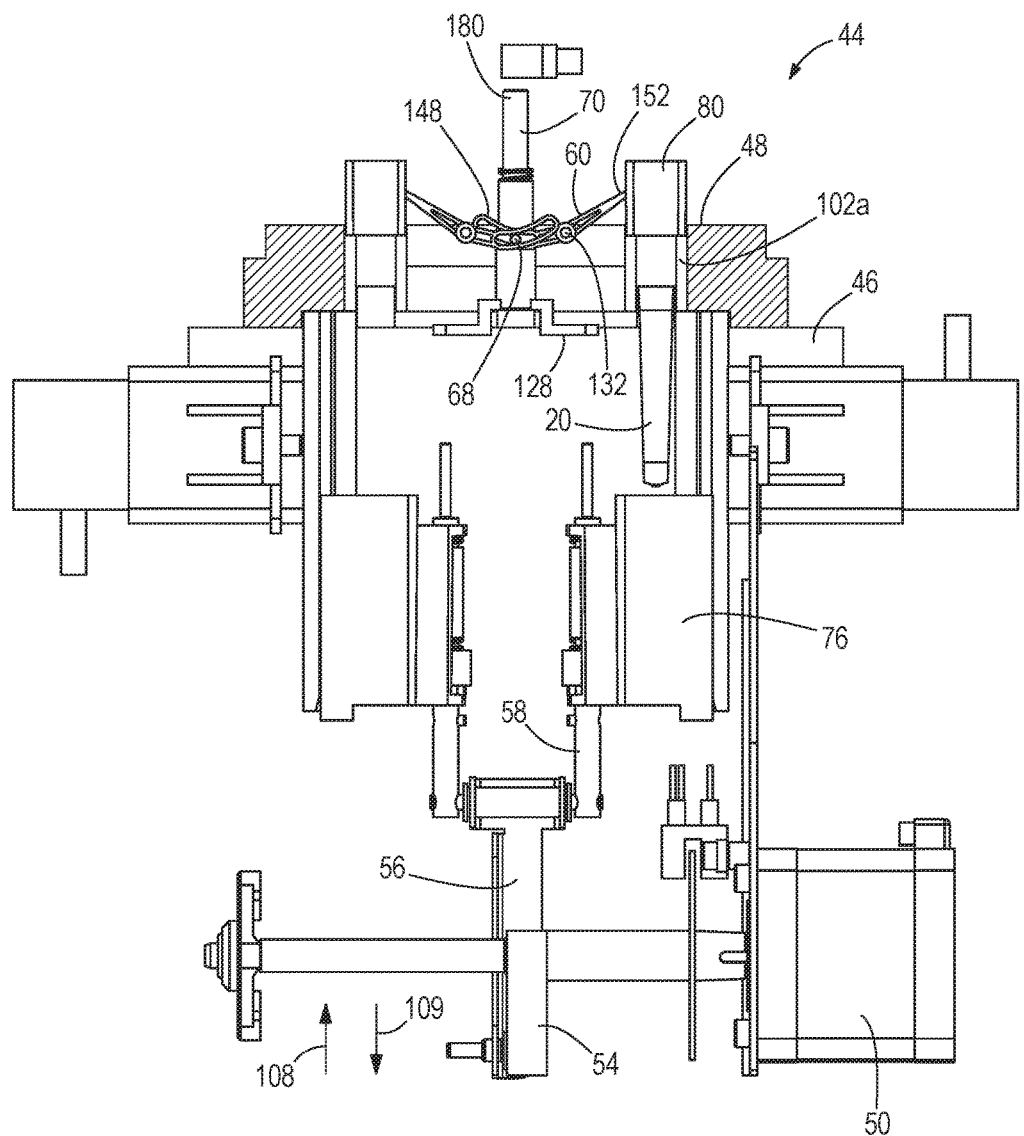
FIG. 8 illustrates a front view of the diagnostic analyzer of FIG. 5 with a first light-blocking member and second light light-blocking members of the testing device disposed in an open position.

FIG. 8 illustrates a front view of the diagnostic analyzer 10 of FIG. 5 with the first light-blocking member 76 and the second light light-blocking members 80 and 84 (hidden from view) of the testing device 44 disposed in an open position (also referred to as the first position). It is noted that the first light-blocking member 78, the second light-blocking members 82 and 86, and the linkage members 59, 62, and 66 of FIGS. 4 and 5 are not shown to simplify the figure. As shown, the motor 50 has rotated so that the linkage members 54, 56, and 58 have moved in downward direction 109 thereby moving the first light-blocking member 76 apart from the bottom housing 46 and disposing the reaction vessels 20 outside of the inner compartments of the first light-blocking member 76.

Due to this downward movement, the linkage member 58 has been removed from contact with the tab 128 of the linkage member 70. Due to the linkage member 70 being biased in the downward direction 109 as a result of biasing member 180 the linkage member 70 has moved in the downward direction 109. This downward movement of linkage member 70 has correspondingly moved linkage member 68 in the downward direction 109 causing attached linkage members 60 and 64 (hidden from view) to pivot relative to the linkage member 68 and relative to the fixed pin 132. This has caused a teeter-totter movement causing top portions 148 and 150 (hidden from view) of linkage members 60 and 64 (hidden from view) to move downwardly in direction 109, and causing bottom portions 152 and 154 (hidden from view) of linkage members 60 and 64 (hidden from view) to move upwardly in direction 108. This upward movement of the bottom portions 152 and 154 (hidden from view) of linkage members 60 and 64 (hidden from view) in direction 108 has caused the respectively attached second light-blocking members 80 and 84 (hidden from view) to also travel upward in direction 108 so that they are disposed in the open position apart from the track 24 (see FIG. 5) and at least partially outside of the top housing 48, and outside of the elongated channels 102a of the top housing 48.

The exact same mirrored movement occurs with respect to the not-shown first light-blocking member 78, the second light-blocking members 82 and 86, and the linkage members 59, 62, and 66, causing the second light-blocking members 82 and 86 to also be disposed in the identical open position apart from the track 24 and at least partially outside of the top housing 48, and outside of the elongated channels 102b of the top housing 48.

Figure 9:
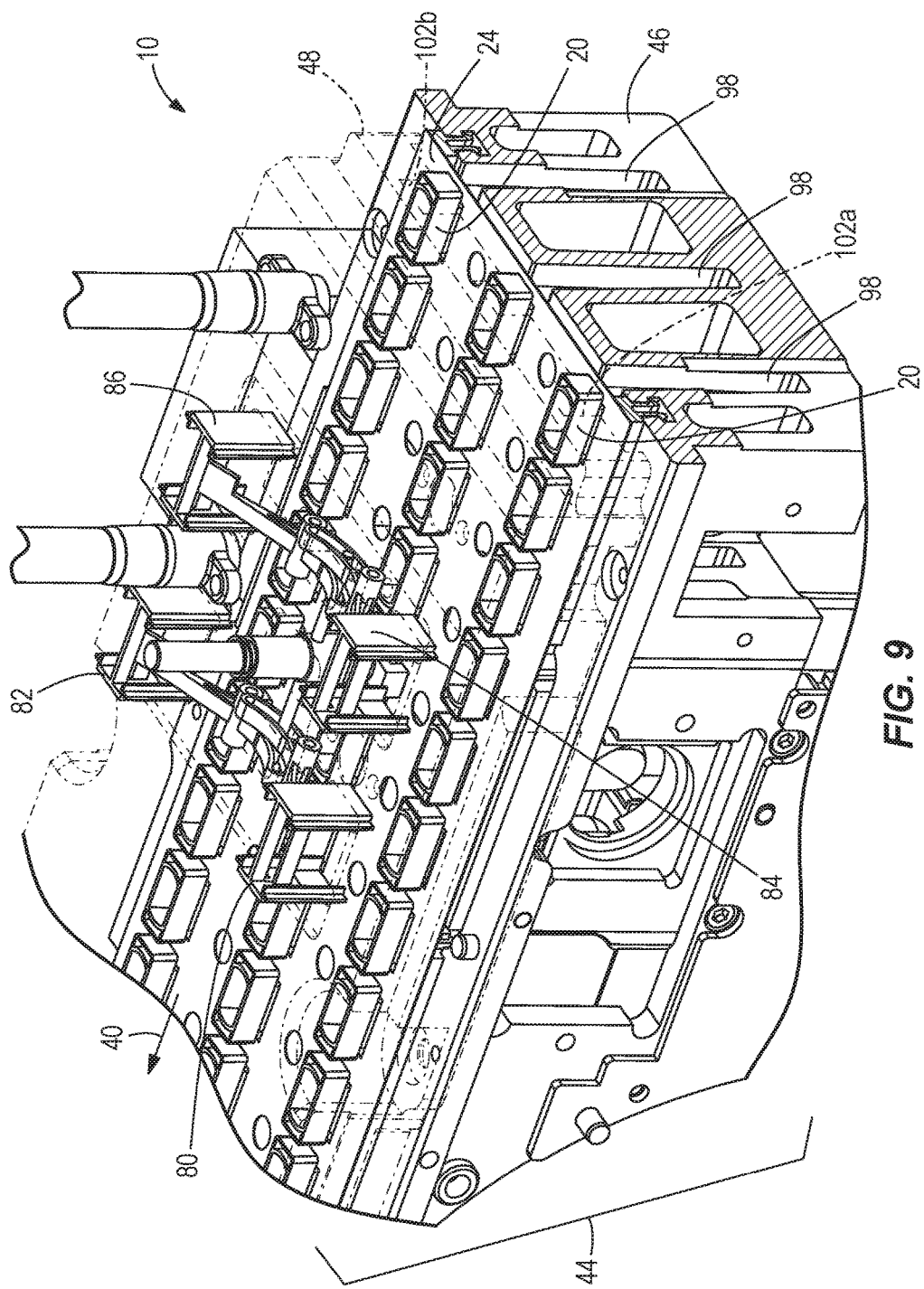
FIG. 9 illustrates a cross-section view through the moving track of the diagnostic analyzer of FIG. 1 with the testing device of FIG. 4 disposed in the open position relative to the moving track.
Figure 10:
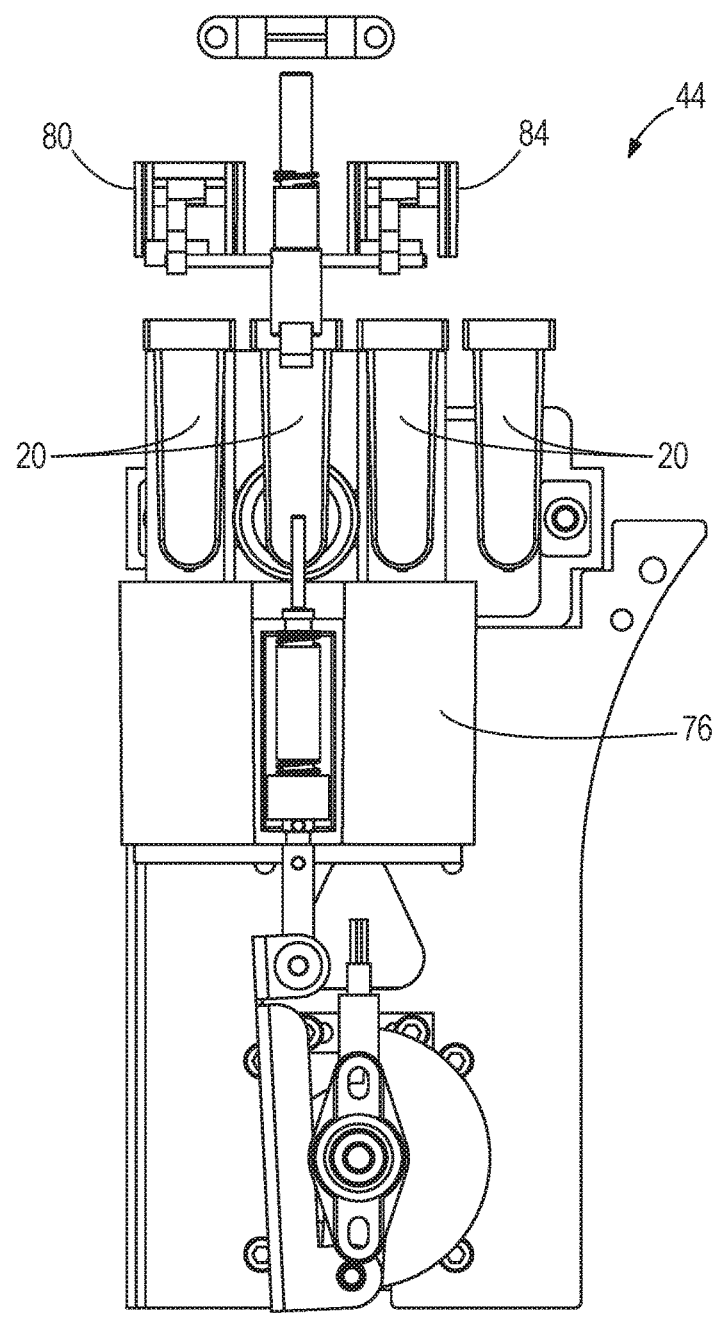
FIG. 10 illustrates a cross-section view through a first light-blocking member and second light-blocking members of the testing device of FIG. 4 while the first light-blocking member and the second light-blocking members are disposed in the open position.

FIG. 9 illustrates a cross-section view through the moving track 24 of the diagnostic analyzer 10 of FIG. 1 with the testing device 44 of FIG. 4 disposed in the open position relative to the moving track 24. FIG. 10 illustrates a cross-section view through the first light-blocking member 76 and the second light-blocking members 80 and 84 of the testing device 44 of FIG. 4 while the first light-blocking member 76 and the second light-blocking members 80 and 84 are disposed in the open position. As shown collectively in FIGS. 8, 9, and 10, the second light-blocking members 80, 82, 84, and 86 are disposed in the open position apart from the track 24, and at least partially outside of the top housing 48, and outside of the elongated channels 102a and 102b of the top housing 48. When the first light-blocking members 76 and 78 (hidden from view) and the second light-blocking members 80, 82, 84, and 86 are disposed in the open positions of FIGS. 8, 9, and 10, the reaction vessels 20 are free to move in direction 40 through the elongated channels 102a and 102b of the top housing 48 and through the elongated channels 98 of the bottom housing 46 as the track 24 moves in direction 40.

Figure 11:
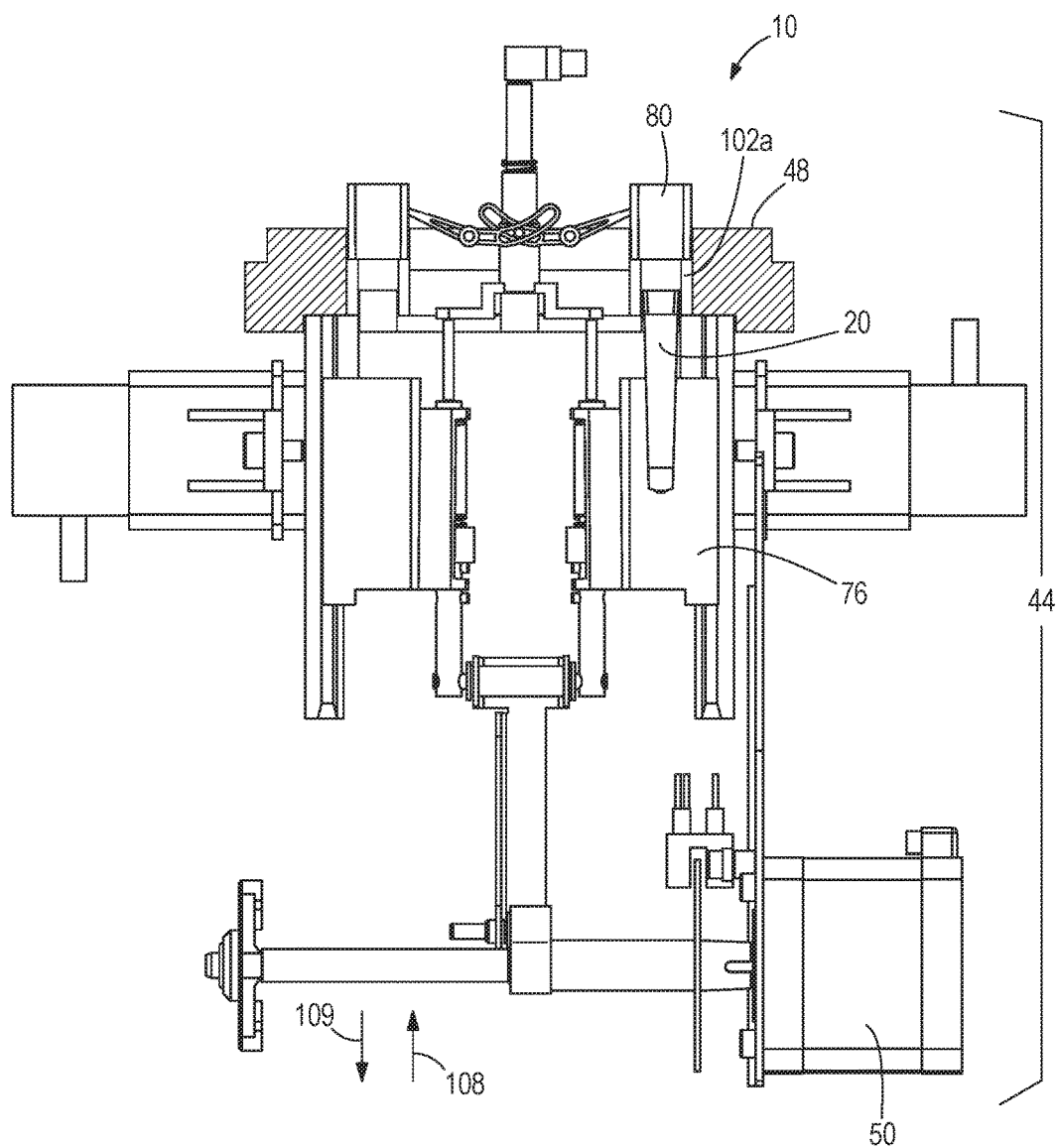
FIG. 11 illustrates a front view of the diagnostic analyzer of FIG. 8 with the first light-blocking member of the testing device having advanced upwardly and the second light-blocking members of the testing device having advanced downwardly as a result of a motor rotating to move the testing device from the open position of FIG. 8 towards the closed position.

FIG. 11 illustrates a front view of the diagnostic analyzer 10 of FIG. 8 with the first light-blocking member 76 of the testing device 44 having advanced upwardly in direction 108, and the second light-blocking members 80 and 84 (hidden from view) of the testing device 44 having advanced downwardly in direction 109 as a result of the motor 50 rotating to move the testing device 44 from the open position of FIG. 8 towards the closed position. The reaction vessels 20 are beginning to be enclosed by the first light-blocking member 76 and the second light-blocking members 80 and 84 (hidden from view) are beginning to at least partially block the elongated channel 102a of the top housing 48. As noted previously, the first light-blocking member 78, the second light-blocking members 82 and 86, and the linkage members 59, 62, and 66 are not shown to simplify the figure.

Figure 12:
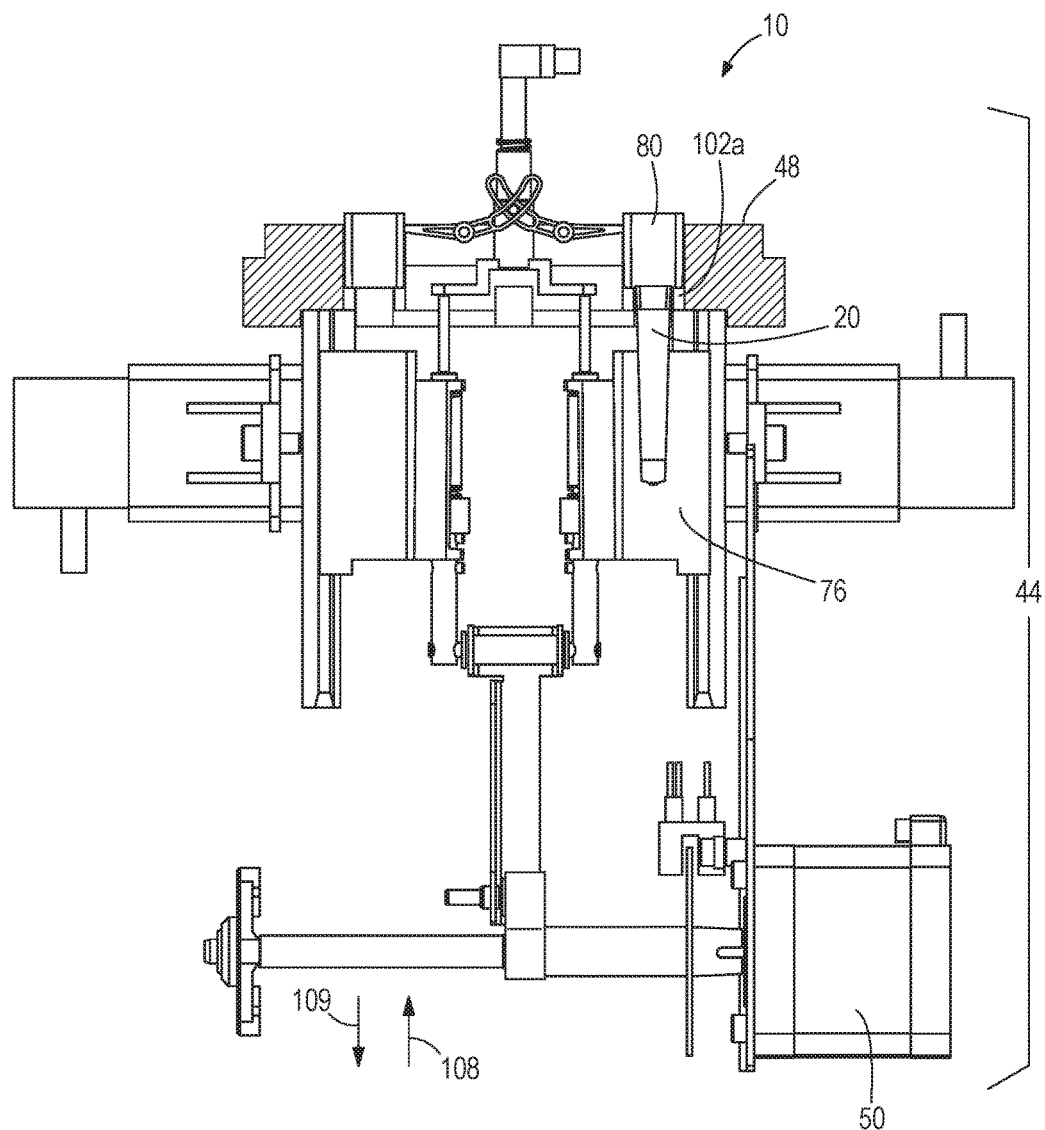
FIG. 12 illustrates a front view of the diagnostic analyzer of FIG. 11 with the first light-blocking member of the testing device having further advanced upwardly and the second light light-blocking members of the testing device having further advanced downwardly as a result of the motor moving the testing device closer to the closed position.

FIG. 12 illustrates a front view of the diagnostic analyzer 10 of FIG. 11 with the first light-blocking member 76 of the testing device 44 having further advanced upwardly in direction 108 and the second light light-blocking members 80 and 84 (hidden from view) of the testing device 44 having further advanced downwardly in direction 109 as a result of the motor 50 rotating to move the testing device 44 closer to the closed position. The reaction vessels 20 are further enclosed by the first light-blocking member 76 and the second light-blocking members 80 and 84 (hidden from view) are further blocking the elongated channel 102a of the top housing 48. As noted previously, the first light-blocking member 78, the second light-blocking members 82 and 86, and the linkage members 59, 62, and 66 are not shown to simplify the figure.

Figure 13:
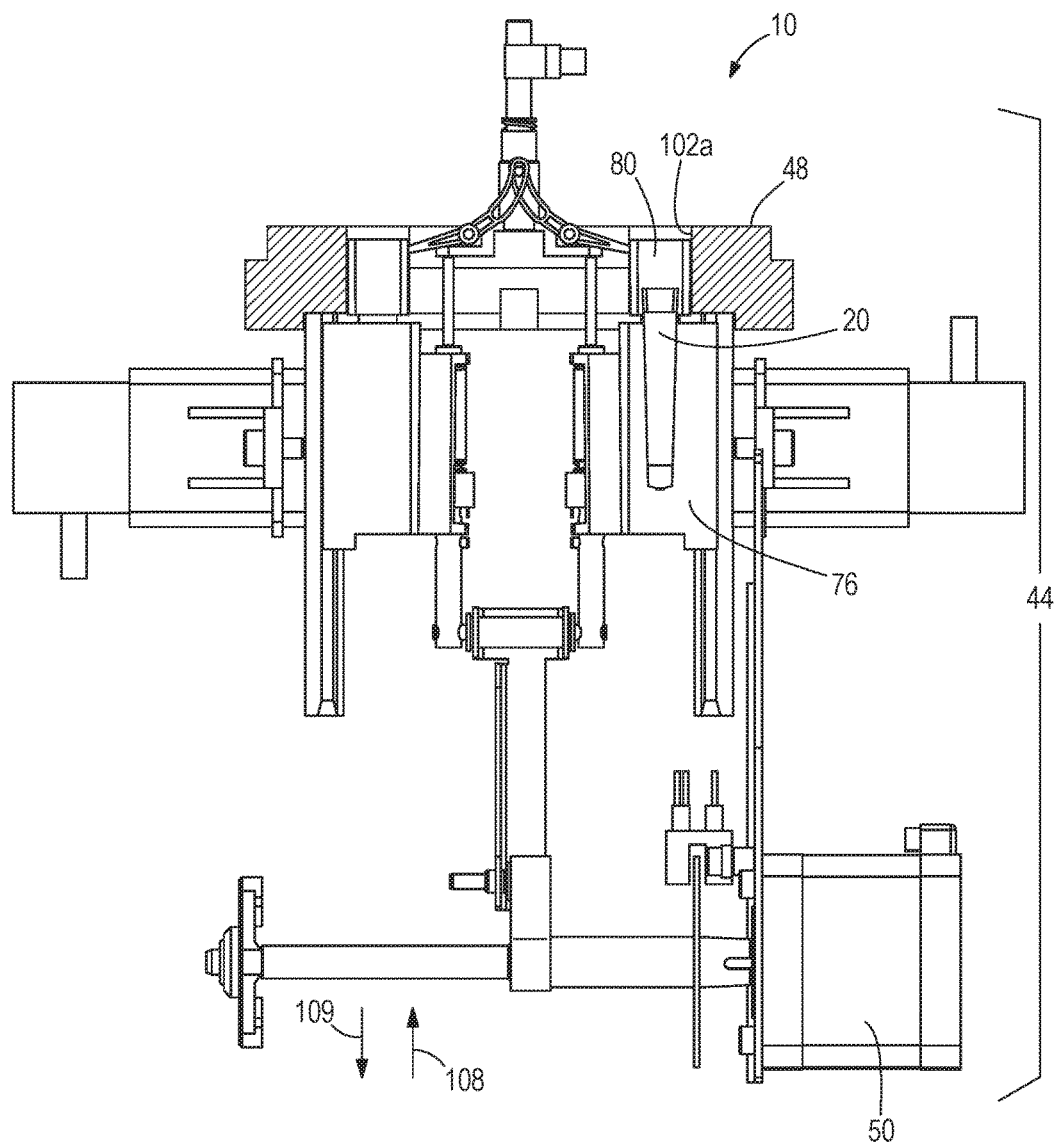
FIG. 13 illustrates a front view of the diagnostic analyzer of FIG. 12 with the first light-blocking member of the testing device having still further advanced upwardly and the second light light-blocking members of the testing device having still further advanced downwardly as a result of the motor rotating to move the testing device closer to the closed position.

FIG. 13 illustrates a front view of the diagnostic analyzer 10 of FIG. 12 with the first light-blocking member 76 of the testing device 44 having still further advanced upwardly in direction 108 and the second light light-blocking members 80 and 84 (hidden from view) of the testing device 44 having still further advanced downwardly in direction 109 as a result of the motor 50 rotating to move the testing device 44 closer to the closed position. The reaction vessels 20 are still further enclosed by the first light-blocking member 76 and the second light-blocking members 80 and 84 (hidden from view) are still further blocking the elongated channel 102a of the top housing 48. As noted previously, the first light-blocking member 78, the second light-blocking members 82 and 86, and the linkage members 59, 62, and 66 are not shown to simplify the figure.

Figure 14:
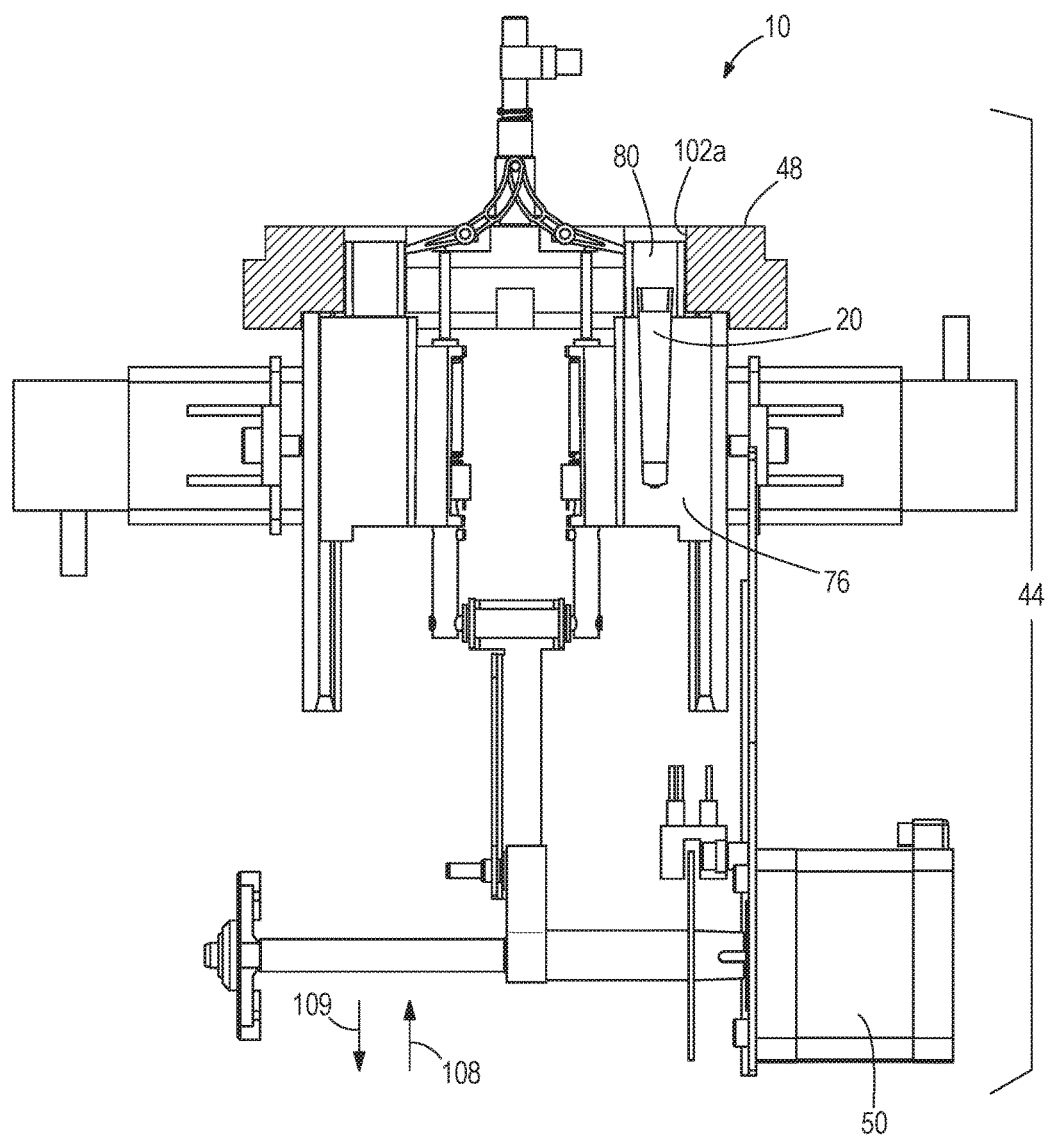
FIG. 14 illustrates a front view of the diagnostic analyzer 10 of FIG. 13 with the first light-blocking member of the testing device having further advanced upwardly to the closed position and the second light light-blocking members of the testing device having further advanced downwardly to the closed position as a result of the motor rotating to move the testing device.

FIG. 14 illustrates a front view of the diagnostic analyzer 10 of FIG. 13 with the first light-blocking member 76 of the testing device 44 having further advanced upwardly in direction 108 to the closed position and the second light light-blocking members 80 and 84 (hidden from view) of the testing device 44 having further advanced downwardly in direction 109 to the closed position as a result of the motor 50 rotating to move the testing device 44. The reaction vessels 20 are completely enclosed by the first light-blocking member 76 and the second light-blocking members 80 and 84 (hidden from view) are blocking the elongated channel 102a of the top housing 48. As noted previously, the first light-blocking member 78, the second light-blocking members 82 and 86, and the linkage members 59, 62, and 66 are not shown to simplify the figure.

By further rotation of the motor 50 the process repeats itself and the testing device 44 can be moved from the closed position of FIG. 14 back through the interim positions of FIGS. 13, 12, and 11 to the open position of FIG. 8. In such manner, the motor 50 can open and close the testing device 44 to allow the reaction vessels 20 to move through the elongated channels 102a and 102b (see FIG. 9) of the top housing 48 and to move through the elongated channels 98 (see FIG. 9) of the bottom housing 46 when the testing device 44 is in the open position, and to block light from entering into the reaction vessel 20 being tested by the optical testing devices 88 and 90 (see FIGS. 4 and 5) when the testing device 44 is disposed in the closed position.

Figure 15:
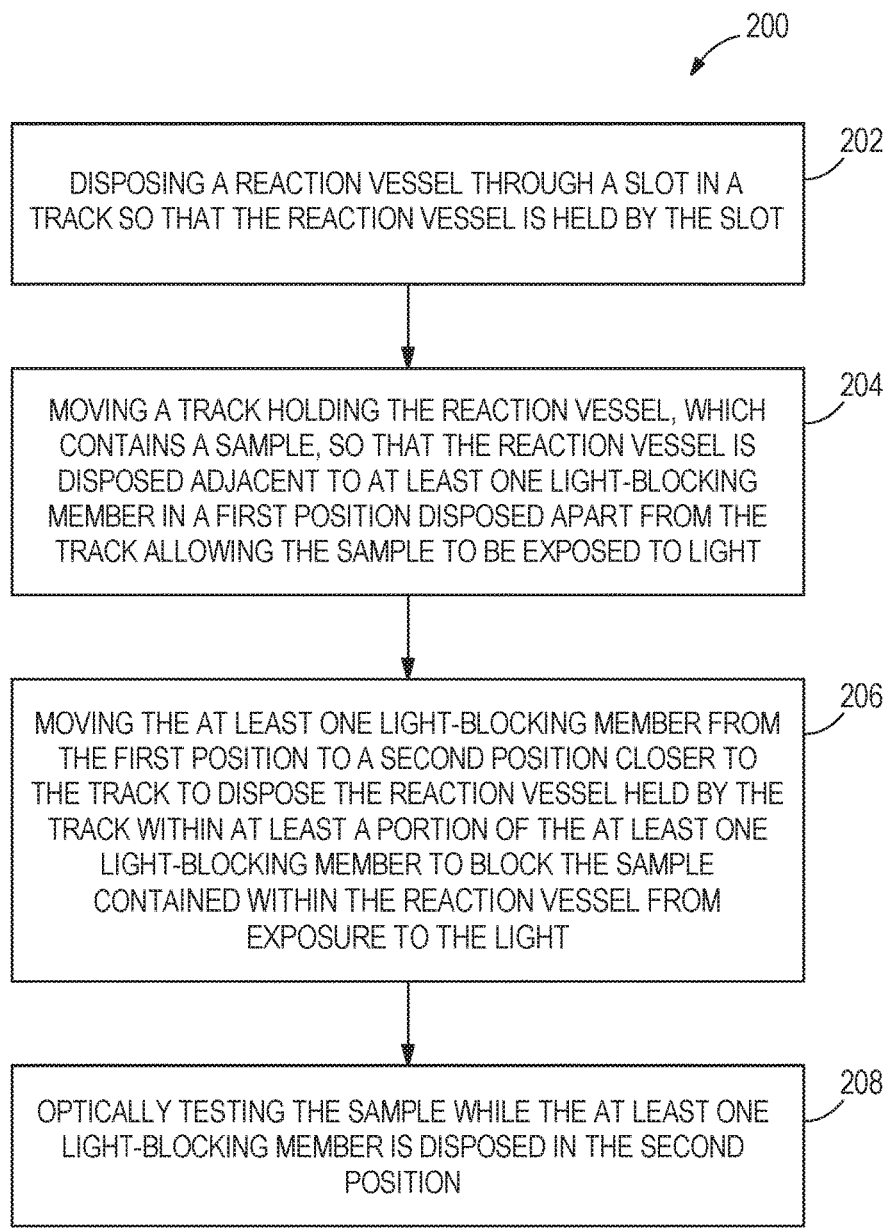
FIG. 15 illustrates one embodiment of a method of diagnostically testing a sample.

FIG. 15 illustrates one embodiment of a method 200 of diagnostically testing a sample. In step 202, a reaction vessel is disposed through a slot in a track so that the reaction vessel is held by the slot. In step 204, a track is moved holding the reaction vessel, which contains a sample, so that the reaction vessel is disposed adjacent to at least one light-blocking member in a first position disposed apart from the track allowing the sample to be exposed to light. The track may be linear. In the first position a first light-blocking member may be disposed below the track and a second light-blocking member may be disposed above the track. The first light-blocking member may comprise an inner compartment having an open top end, and the second light-blocking member may comprise a shutter. In the first position the first light-blocking member may be disposed under the track apart from an elongated channel of a bottom housing with the elongated channel holding a bottom portion of the reaction vessel. In the first position the second light-blocking member may be disposed over the track apart from an elongated channel of a top housing with the elongated channel holding a top portion of the reaction vessel. In the first position samples contained within reaction vessels, held on opposite sides of the track, may be exposed to light.

In step 206, the at least one light-blocking member is moved from the first position to a second position closer to the track to dispose the reaction vessel held by the track within at least a portion of the at least one light-blocking member to block the sample contained within the reaction vessel from exposure to the light. This step may comprise moving the first and the second light-blocking members with a motor connected to a plurality of linkage members which are connected to the first and second light-blocking members. This step may further comprise moving the first light-blocking member relative to an attached frame member so that an optical reader of an optical testing device is disposed, when in the second position, adjacent to an inner compartment formed between the first light-blocking member and the attached frame member.

In the second position the first and second light-blocking members may at least partially close around the reaction vessel to block the sample contained within the reaction vessel from exposure to the light. In the second position the first light-blocking member may be disposed against a bottom surface of the track and the second light-blocking member may be disposed against a top surface of the track. In the second position the first light-blocking member may be disposed under the track within the elongated channel around the bottom portion of the reaction vessel. In the second position the second light-blocking member may be disposed within the elongated channel against the top portion of the track and adjacent to a side of the reaction vessel. In the second position a bottom portion of the reaction vessel may be disposed in an inner compartment of the first light-blocking member below a bottom portion of the track.

In the second position a shutter of the second light-blocking member may be disposed against a top portion of the track in-between the reaction vessel and a second reaction vessel held by the track with the shutter blocking the sample from exposure to the light from a second sample disposed within the second reaction vessel. In the second position a bottom portion of the reaction vessel may be disposed in one of a plurality of inner compartments of the first light-blocking member below a bottom portion of the track. In the second position a plurality of shutters of the second light-blocking member may be disposed on opposite sides of the reaction vessel against a top portion of the track in-between the reaction vessel and additional reaction vessels held by the track with the plurality of shutters blocking the sample from exposure to the light from additional samples disposed within the additional reaction vessels. In the second position each of separate respective light-blocking members disposed at opposite sides of the track may block the samples contained within the reaction vessels, held on the opposite sides of the track, from exposure to the light.

In step 208, the sample is optically tested while the at least one light-blocking member is disposed in the second position. Step 208 may comprise conducting a chemiluminescence test on the sample. In other embodiments of the method 200, one or more of the steps may be modified in substance or order, one or more of the steps may not be followed, or one or more steps may be added.

One or more embodiments of the disclosure may reduce one or more issues of one or more of the existing diagnostic analyzers by: increasing throughput of the diagnostic analyzer as a result of the samples being tested directly on the processing path; taking up less space as a result of the testing device being located directly on the processing path of the linear track of the diagnostic analyzer; and reducing manufacturing cost as a result of the simple and relatively inexpensive testing device of the diagnostic analyzer of the disclosure.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the disclosure is defined by the appended claims. Accordingly, the disclosure is not to be restricted except in light of the appended claims and their equivalents.

The invention claimed is:

1. A diagnostic analyzer comprising:
    a track configured to move a reaction vessel held by the track;
    at least one light-blocking member disposed adjacent to the track, the at least one light-blocking member configured to move from a first position apart from the track to a second position closer to the track, wherein when the at least one light-blocking member is disposed in the first position a sample contained within the reaction vessel held by the track is exposed to light, and when the at least one light-blocking member is disposed in the second position the sample contained within the reaction vessel held by the track is blocked from exposure to the light by the at least one light-blocking member;
    a motor configured to move the at least one light-blocking member between the first and the second positions; and
    an optical testing device disposed adjacent to the track and configured to optically test the sample contained within the reaction vessel held by the track when the at least one light-blocking member is disposed in the second position blocking the sample from exposure to the light.

2. The diagnostic analyzer of claim 1 wherein the at least one light-blocking member comprises a first light-blocking member and a second light-blocking member, wherein in the second position the first and the second light-blocking members at least partially close around the reaction vessel to block the sample contained within the reaction vessel from exposure to the light.

3. The diagnostic analyzer of claim 2 wherein the track further comprises a slot disposed through the track, the reaction vessel extending through the slot so that a top portion of the reaction vessel is disposed above the track and a bottom portion of the reaction vessel is disposed below the track.

4. The diagnostic analyzer of claim 2 wherein in the first position the first light-blocking member is disposed below the track and the second light-blocking member is disposed above the track.

5. The diagnostic analyzer of claim 2 wherein in the second position the first light-blocking member is disposed against a bottom surface of the track and the second light-blocking member is disposed against a top surface of the track.

6. The diagnostic analyzer of claim 2 further comprising a bottom housing disposed under the track, the bottom housing comprising an elongated channel sized to hold a bottom portion of the reaction vessel, wherein in the first position the first light-blocking member is disposed under the track apart from the elongated channel and in the second position the first light-blocking member is disposed under the track within the elongated channel around the bottom portion of the reaction vessel.

7. The diagnostic analyzer of claim 2 further comprising a top housing disposed over the track, the top housing comprising an elongated channel sized to hold a top portion of the reaction vessel, wherein in the first position the second light-blocking member is disposed over the track apart from the elongated channel and in the second position the second light-blocking member is disposed within the elongated channel against the top portion of the track and adjacent to a side of the reaction vessel.

8. The diagnostic analyzer of claim 2 wherein the first and the second light-blocking members are connected by a plurality of linkage members, and the motor is connected to the plurality of linkage members.

9. The diagnostic analyzer of claim 2 wherein the first light-blocking member comprises an inner compartment having an open top end, and the second light-blocking member comprises a shutter, wherein in the second position a bottom portion of the reaction vessel is disposed in the inner compartment of the first light-blocking member below a bottom portion of the track and the shutter is disposed against a top portion of the track in-between the reaction vessel and a second reaction vessel held by the track with the shutter blocking the sample from exposure to the light from a second sample disposed within the second reaction vessel.

10. The diagnostic analyzer of claim 2 wherein the first light-blocking member is moveably attached to a frame member, wherein in the second position an inner compartment formed between the first light-blocking member and the frame member is disposed adjacent to an optical reader of the optical testing device.

11. The diagnostic analyzer of claim 1 wherein the track comprises a continuous track disposed around pulleys.

12. The diagnostic analyzer of claim 1 wherein the at least one light-blocking member is configured to move vertically.

13. The diagnostic analyzer of claim 2 wherein the first light-blocking member and the second light-blocking member are each configured to move vertically.

14. The diagnostic analyzer of claim 1 wherein the at least one light-blocking member is entirely disposed either above or below the track.

15. The diagnostic analyzer of claim 2 wherein the first light-blocking member is entirely disposed below the track, and the second light-blocking member is entirely disposed above the track.

* * * * *